US012649886B2

(12) United States Patent
Huber et al.

(10) Patent No.: US 12,649,886 B2
(45) Date of Patent: Jun. 9, 2026

(54) PROCESS FOR MAKING ETHERS FROM ETHANOL

(71) Applicants: Wisconsin Alumni Research Foundation, Madison, WI (US); The Trustees of Princeton University, Princeton, NJ (US)

(72) Inventors: George Huber, Middleton, WI (US); Emmanuel Canales, Madison, WI (US); Christos Maravelias, Princeton, NJ (US); Juan Manuel Restrepo Florez, Madison, WI (US); Javier Chavarrio, Madison, WI (US)

(73) Assignees: Wisconsin Alumni Research Foundation, Madison, WI (US); The Trustees of Princeton University, Princeton, NJ (US)

( * ) Notice: Subject to any disclaimer, the term of this patent is extended or adjusted under 35 U.S.C. 154(b) by 43 days.

(21) Appl. No.: 18/475,328

(22) Filed: Sep. 27, 2023

(65) Prior Publication Data

US 2025/0101326 A1 Mar. 27, 2025

(51) Int. Cl.

*C10L 1/02* (2006.01)
*C07C 2/06* (2006.01)
*C07C 37/16* (2006.01)
*C07C 41/09* (2006.01)

(52) U.S. Cl.

CPC ................ *C10L 1/026* (2013.01); *C07C 2/06* (2013.01); *C07C 37/16* (2013.01); *C07C 41/09* (2013.01); *C10L 2200/0446* (2013.01)

(58) Field of Classification Search

CPC ...... C10L 1/06; C10L 2200/0446; C07C 2/06; C07C 37/16; C07C 41/09
See application file for complete search history.

(56) References Cited

U.S. PATENT DOCUMENTS

2003/0022947 A1 1/2003 McAtee et al.
2015/0246863 A1* 9/2015 Dubois .................. C10L 1/023 585/329
2021/0363085 A1* 11/2021 Eagan ..................... C07C 29/34

FOREIGN PATENT DOCUMENTS

EP 4141090 A1 * 3/2023 ........... C07C 29/145
WO WO 2023/033692 A1 3/2023

OTHER PUBLICATIONS

Eagan et al., "Catalytic synthesis of distillate-range ethers and olefins from ethanol through Guerbet coupling and etherification", Green Chem., vol. 21 (2019), pp. 3300-3318 (Year: 2019).*
International Search Report and Written Opinion dated Dec. 2, 2024, for PCT Application No. PCT/US2024/048372.
ASTM D975-20c, Standard specification for diesel fuel, 2014.

(Continued)

*Primary Examiner* — Latosha Hines
(74) *Attorney, Agent, or Firm* — Joseph T. Leone; Yanjun Ma; DeWitt LLP

(57) ABSTRACT

A process for making liquid fuels, especially diesel fuel, from primary alcohols. The process involves subjecting a feedstock comprising primary alcohols to Guerbet coupling to yield a first intermediate mix; subjecting the first intermediate mix to hydrogenolysis to yield a second intermediate mix; and subjecting the second intermediate mix to etherification to yield a liquid fuel suitable for use in internal combustion engines.

18 Claims, 15 Drawing Sheets

(56) References Cited

OTHER PUBLICATIONS

Cuello-Penaloza et al., "Reaction chemistry of ethanol oligomerization to distillate-range molecules using low loading Cu/MgxAlOy catalysts," Appl Catal B, Dec. 5, 2022, 318, 121821.
Dagle et al., Ethanol as a renewable building block for fuels and chemicals, Ind Eng Chem Res, 2020, 59, 4843-4853.
Dahmen and Marquardt, Model-Based Formulation of Biofuel Blends by Simultaneous Product and Pathway Design, Energy and Fuels, 2017, 31, 4096-4121.
Davis et al. Net-zero emissions energy systems, Science (1979), 2018, 360, 1419.
Doe, Biodiesel Income Tax Credit. U.S. Department of Energy—Energy Efficiency and Renewable Energy Alternative Fuels Data Center.
Eagan, et al., Catalytic synthesis of distillate-range ethers and olefins from ethanol through Guerbet coupling and etherification, Green Chemistry, 2019, 21, 3300-3318.
EIA, Annual energy outlook 2021, Washington DC, 2021, vol. 2021.
EIA, Monthly energy review—Jun. 2021, Washington DC, 2021, vol. 159.
EPA, Greenhouse Gases Equivalencies Calculator—Calculations and References, epa.gov/energy/greenhouse-gases-equivalencies-calculator-calculations-and-references.
EPA, Overview for Renewable Fuel Standard, epa.gov/renewable-fuel-standard-program/overview-renewable-fuel-standard.
EPA, RIN trades and price information, epa.gov/fuels-registration-reporting-and-compliance-help/rin-trades-and-price-information, (accessed Sep. 25, 2022).
Gaspar, D. J. (2021) "Top 13 Blendstocks Derived from Biomass for Mixing-Controlled Compression-Ignition (Diesel) Engines: Bioblendstocks with Potential for Lower Emissions and Increased Operability," PNNL-31421, Pacific Northwest National Laboratory, Richland, WA.
Humbird, et al., Process Design and Economics for Biochemical Conversion of Lignocellulosic Biomass to Ethanol: Dilute-Acid Pretreatment and Enzymatic Hydrolysis of Corn Stover, Golden, Colorado, 2011.
Huq et al., Performance-advantaged ether diesel bioblendstock production by a priori design, Proc Natl Acad Sci USA, 2019, 116, 26421-26430.
Keshwani and Cheng, Switchgrass for Bioethanol and Other Value-Added Applications: A Review Bioresour Technol, 2009, 100, 1515-1523.
Kieboom and van Randwijk, "Hydrogenation and hydrogenolysis in synthetic organic chemistry," © 1977 : Springer Press, NY, NY; ISBN-13: 978-9029801010.
Kim et al. Synthesis of Copper Nano-Ink in Alcohol Media, 2010 Jpn. J. Appl. Phys. 49 05EA04; DOI: 10.1143/JJAP.49.05EA04.
Larina O. V, Valihura K. V, Kyriienko P. I, Vlasenko N. V, Balakin D. Y, Khalakhan I, Čendak T, Soloviev S. O and Orlyk S. M, Appl Catal A Gen, 2019, 588, 1-11.
Ou et al., Life-cycle analysis of energy use and greenhouse gas emissions of gas-to-liquid fuel pathway from steel mill off-gas in China by the LanzaTech process, Frontiers in Energy, 2013, 7, 263-270.
Phung T. K, Copper-based catalysts for ethanol dehydrogenation and dehydrogenative coupling into hydrogen, acetaldehyde and ethyl acetate, Int J Hydrogen Energy, 2022, 47, 42234-42249.
Restrepo-Florez et al. Advanced diesel from ethanol: a pathway to produce sustainable and high-quality drop-in biofuels. Sustainable Energy & Fuels, 2024. pp. 1-17.
Restrepo-Florez et al. (2023) "Ethanol to diesel: a sustainable alternative for the heavy-duty transportation sector," Sustainable Energy Fuels, 7:693-707; DOI:10.1039/d2se01377k.
Rorrer et al., Synthesis of Biomass-Derived Ethers for Use as Fuels and Lubricants, ChemSusChem, 2019, 12, 2835-2858.
Sarkar et al., Bioethanol production from agricultural wastes: An overview, Renew Energy, 2012, 37, 19-27.
Schittkowski et al. On the bifunctional nature of $Cu/ZrO_2$ catalysts applied in the hydrogenation of ethyl acetate, J Catal, 2017, 352, 120-129.
Tsuchida T, Kubo J, Yoshioka T, Sakuma S, Takeguchi T. and Ueda W, Reaction of ethanol over hydroxyapatite affected by Ca/P ratio of catalyst, J Catal, 2008, 259, 183-189.
Zhang et al., Synergistic interaction between Cu and ZrO2 promotes ethyl formate hydrogenation to produce methanol, Catal Today, 2021, 374, 53-60.

* cited by examiner

PROCESS FOR MAKING ETHERS FROM ETHANOL

FEDERAL FUNDING STATEMENT

This invention was made with government support under DE-EE0008480 awarded by the US Department of Energy. The government has certain rights in the invention.

BACKGROUND

The consumption of diesel fuel is projected to remain constant in the U.S. at ~4 million barrels per day for the next 30 years. (EIA, *Annual energy outlook* 2021, Washington DC, 2021, vol. 2021.) With a $CO_2$ emission factor of 10.18 kg/gal, this consumption generates daily $CO_2$ emissions of ~1.7 million tons. (EPA, Greenhouse Gases Equivalencies Calculator—Calculations and References, epa.gov/energy/greenhouse-gases-equivalencies-calculator-calculations-and-references. Diesel fuel is mostly used in ships, trucks, and heavy-duty equipment. Unlike light-duty vehicles, this heavy-duty equipment is challenging to electrify, making cargo transport a difficult to decarbonize sector. Biofuels may play a significant role in these applications. First, the energy density of biofuels is only slightly lower than fossil fuels. Second, no change in the fuel distribution infrastructure is required. In the U.S., a significant amount of research has been devoted to analyzing different renewable diesel production pathways. See Table 1 and Gaspar, D. J. (2021) "Top 13 Blendstocks Derived from Biomass for Mixing-Controlled Compression-Ignition (Diesel) Engines: Bioblendstocks with Potential for Lower Emissions and Increased Operability," PNNL-31421, Pacific Northwest National Laboratory, Richland, WA. See also Restrepo-Florez et al. (2023) "Ethanol to diesel: a sustainable alternative for the heavy-duty transportation sector," *Sustainable Energy Fuels,* 7:693-707; DOI:10.1039/d2se01377k. These efforts have been focused on identifying biofuel alternatives that satisfy three requirements: (1) economic feasibility; (2) low greenhouse gas emissions (<60% than fossil diesel); and (3) operability. The last of these requirements has been assessed by the fuel properties, which should be equal or superior to those of fossil diesel.

TABLE 1

Main pathways for producing renewable diesel fuel from biomass (adapted from Gaspar et al. 2021 and Restrepo-Florez et al. 2023).

| | CN [—] | Flash point [° C.] | Cloud point [° C.] | Energy Density [MJ/L] | Viscosity [$mm^2/s$] | Density [$Kg/m^3$] | MFSP [$/GDE] * | ΔGHG [%] |
|---|---|---|---|---|---|---|---|---|
| Diesel | >40 | >52 | | ~35 | 1.9-4.1 | >820 | 1.8-3.5** | [—] |
| Renewable diesel HEFA | >70 | >61 | −39 | 34.4 | 2-4 | 770-790 | 4.7-7.8 | 60-80 |
| Fischer Tropsch Diesel | >70 | >61 | −34 to 10 | 34 | 2-4 | 770-790 | 5.5 | 89 |
| HTL fuel | 30-68 | >55 | −60 to 20 | 34.5-36.9 | 2.3-2.7 | 800-879 | 4.3-6.7 | 62-73 |
| Farnesane | 58.6 | 110 | −73 | 33.5 | 14 | 773 | 7.8-9.4 | 61 |
| Isoalkanes from VFA | 48 | 74 | −80 | 34.6 | 1.49 | 780 | 12.5 | <60% |
| Ethanol-to-distillate | 55-68 | >54 | −60.1 | 35 | 2.0-4.8 | 786 | 4.7-7.2 | >90% |
| Biodiesel | >47 | >93 | −5 to 15 | 33 | 1.9-6 | 880 | 5.3 | 39-90 |
| Fatty acid fusel esters | 50-60 | >130 | −10 | >30 | 2.9-3.7 | 817-861 | 3.8-5.3 | 53% |
| Short chain esters from oilseed crops | 52 | 111 | −18 | 29.6 | 1.7 | 871 | 25.1 | 20-53 |
| Polyoxymethylene ethers | 73-75 | 62-63 | −27-19 | 20-32 | 1.9 | 1.0662 | 6.4-7 | 81 |
| 4-butoxyheptane | 80 | 64 | −80 | 30.8 | 0.795 | 791 | 11.0 | 27 |
| Alkoxyalkanoates from lactate esters | 44-62 | 65-117 | <−50 | 23-33 | 1.2-2.3 | 900-930 | 7.8 | 65 |
| Fatty alkyl ethers | 74-104 | >150 | −5 to−16 | 34-36 | | 830-850 | 6.3 | 57-75 |
| Ethanol upgrading by Guerbet coupling and etherification | 73.2 | >50 | −37 | 27.5 | 1.92 | 815 | 4-7.7 | >50 |

* MFSP is in 2021 dollars;
**Diesel spot price
MFSP: Minimum Fuel Selling Price, ΔGHG: reduction in greenhouse gas emissions in comparison with fossil diesel.

Among the pathways in Table 1, ethanol upgrading by Guerbet coupling and etherification is of particular interest. (Restrepo-Flórez et al. 2023.) This pathway has several advantages in terms of fuel properties, greenhouse gas (GHG) emission reductions, and feedstock availability, while simultaneously showing technoeconomic feasibility. From a fuel property perspective, it has been demonstrated that it is possible to produce renewable diesel #2 that satisfies most ASTM requirements with significant improvements in cetane number (>70), and cold flow properties (cloud point <−37° C.). This outstanding behavior is the result of using an ether-rich blend as diesel. Ethers are known for their high cetane number and have been identified as a potential diesel replacement in several studies. See Huq et al., *Proc Natl Acad Sci USA,* 2019, 116, 26421-26430; Rorrer et al, *Chem Sus Chem,* 2019, 12, 2835-2858; and Dahmen and Marquardt, *Energy and Fuels,* 2017, 31, 4096-4121.

In terms of GHG mitigation potential, the possibility of obtaining more than 60% reduction in comparison with fossil diesel has been shown. Furthermore, depending on the carbon intensity of the ethanol used, it is possible to produce carbon neutral or carbon negative diesel. A pathway based on ethanol upgrading is particularly well positioned in terms of feedstock availability in comparison with other alternatives. There is already infrastructure in the U.S. with a production capacity close to 17 billion gallons per year. See Dagle et al., *Ind Eng Chem Res,* 2020, 59, 4843-4853 and EIA, *Monthly energy review—June* 2021, Washington DC, 2021, vol. 159. Additionally, there are emerging technologies (e.g., fermentation of lignocellulosic residues or syngas) that may disrupt the ethanol market by increasing the supply while reducing the environmental impacts of ethanol production and/or its production costs. See Humbird, et al., *Process Design and Economics for Biochemical Conversion of Lignocellulosic Biomass to Ethanol: Dilute-Acid Pretreatment and Enzymatic Hydrolysis of Corn Stover,* Golden, Colorado, 2011; Keshwani Cheng, *Bioresour Technol,* 2009, 100, 1515-1523; Sarkar et al., *Renew Energy,* 2012, 37, 19-27; and Ou et al., *Frontiers in Energy,* 2013, 7, 263-270.

Despite the advantages of ethanol upgrading via Guerbet coupling and etherification, three limitations hindering the deployment of this technology have been identified: (1) the Guerbet coupling reaction of ethanol has as a main product 1-butanol. Eagan, et al., *Green Chemistry,* 2019, 21, 3300-3318. The overabundance of 1-butanol in the etherification reaction leads to the production of a significant fraction of dibutyl ether, with a flash point (25° C.) well below diesel #2 requirements (>52° C.). Consequently, the yield of diesel #2 is reduced to a maximum of ~50%. (Restrepo-Florez et al. 2023.) (2) The most effective Guerbet coupling catalysts for diesel production purposes (i.e., those that produce the highest amount of C6+ alcohols) also produce significant amounts of esters, aldehydes, and ketones. Esters significantly affect the ether selectivity in etherification reactions, while the aldehydes and ketones produced are not suitable to be used in diesel due to their physicochemical properties. (The aldehydes and ketones are mostly small molecules; they have unsuitably low cetane numbers and flash points). (3) While it is expected that the diesel #2 produced by Guerbet coupling and etherification would reduce the emission profile in comparison with diesel fuel, there is no characterization of the engine performance of these blends.

Thus there remains a long-felt and unmet need for a more efficient method to upgrade of ethanol into diesel.

SUMMARY

Disclosed herein is a process for making liquid fuels, especially diesel fuel. The process comprises:

(a) subjecting a feedstock comprising primary alcohols to Guerbet coupling to yield a first intermediate mix;

(b) subjecting at least a portion of the first intermediate mix to hydrogenolysis to yield a second intermediate mix;

(c) subjecting at least a portion of the second intermediate mix to etherifcation to yield a liquid fuel.

In step (a), the Guerbet coupling is conducted such that the first intermediate mix comprises alcohols higher in molecular weight than the primary alcohols in the feedstock. In step (b), the hydrogenolysis is conducted such that at least a portion of aldehydes, ketones, and esters present in the first intermediate mix are converted to their analogous alcohols. In step (c), the etherification is conducted such that at least a portion of alcohols present in the second intermediate mix are converted to ethers whose molecular weight is suitable for use as diesel fuel.

Optionally, at least a portion of unreacted alcohol from step (b) is separated from the second intermediate product mix and recycled into the feedstock used in step (a). This makes the overall process far more efficient. When in step (a) the feedstock comprises ethanol, some or all of the unreacted ethanol and some or all of the butanol produced by the Guerbet coupling and hydrogenolysis may optionally be separated from the second intermediate product mix and recycled into the feedstock used in step (a). Again, recycling some or all of the unreacted ethanol and some or all of the produced butanol increased the overall yield of the final, liquid fuel product.

In another version of the process, the second intermediate mix is fractionated into a heavy cut comprising alcohols having 10 or more carbon atoms and a light cut comprising alcohols having from 4 to 9 carbon atoms. The heavy cut can be used as the liquid fuel product itself or mixed with the liquid fuel product resulting from step (c) of the process. The light cut is used as the feedstock for the etherification reaction of step (c).

The Guerbet coupling reaction may be catalyzed with a catalyst comprising an oxide selected from the group consisting of Mg, Ca, Zn, Mn, Sr, Si, Zr, Al, La, Ga, Ce, Fe, Sc, Cr, P, and V. The catalyst may optionally comprise a metal selected from the group consisting of Cu, Ni, Pt, Pd, Rh, Co, Cs, and Rb. The listed oxides and metals are non-exclusive; any material capable of catalyzing a Guerbet coupling reaction may be used. Likewise, the hydrogenolysis reaction may be catalyzed using a catalyst comprising a metal selected from the group consisting of Cu, Ni, Rh, Ru, Ir, and Pd. The list is non-exclusive.

In an optional fourth step (d) comprises oligomerizing at least a portion of the olefins created by the Guerbet step (a) or etherification of step (c). This increases their molecular weight to a range more suitable for use in diesel fuel.

A preferred version of the process comprises:

(a) subjecting a feedstock comprising ethanol to Guerbet coupling to yield a first intermediate mix comprising butanol;

(b) subjecting at least a portion of the first intermediate mix to hydrogenolysis under conditions wherein at least a portion of aldehydes and ketones present in the first intermediate mix are converted to their analogous alcohols, to yield a second intermediate mix;

(c) subjecting at least a portion of the second intermediate mix to etherifcation under conditions wherein at least a portion of alcohols present in the second intermediate mix are converted to ethers to yield diesel fuel.

Again, a portion of unreacted methanol and a portion of butanol may optionally separated from the second intermediate product mix and recycled into the feedstock used in step (a). This version of the process may also include fractionating the second intermediate mix into a heavy cut and a light cut as described above and using the light cut as a feedstock for the etherification reaction of step (c).

DETAILED DESCRIPTION

Figure 1:
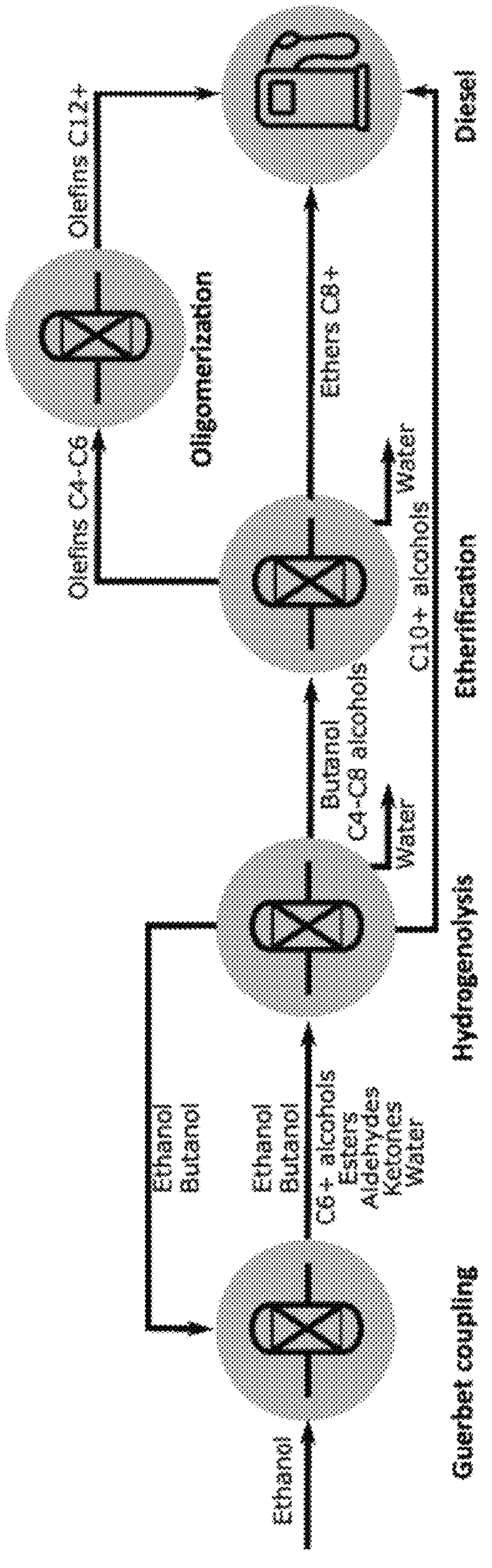
FIG. 1. Schematic of transformation of ethanol into diesel according to the present disclosure.

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any methods and materials similar or equivalent to those described herein can also be used in the practice or testing of the present disclosure, the preferred methods and materials are now described. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation.

As used herein, the singular forms "a." "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

As used herein, the term "about" refers to ±10% of the variable referenced.

As used herein, the term "or" is an inclusive "or" operator and is equivalent to the term "and/or" unless the context clearly dictates otherwise. Unless otherwise clear from context, all numerical values provided herein can be modified by the term "about."

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

The elements and method steps described herein can be used in any combination whether explicitly described or not, unless otherwise specified or clearly implied to the contrary by the context in which the referenced combination is made.

All combinations of method steps as used herein can be performed in any order, unless otherwise specified or clearly implied to the contrary by the context in which the referenced combination is made.

The system disclosed herein may comprise, consist of, or consist essentially of the various steps and elements disclosed herein. The disclosure provided herein may be practiced in the absence of any element or step which is not specifically disclosed herein.

Overview of the Process

Disclosed herein is a process for transforming a primary alcohol (e.g., ethanol, 1-propanol, 1-butanol, etc.) into a blend of components (mainly long chain ethers) that can be used as diesel fuel. The process comprises: (1) a Guerbet coupling step in which the primary ethanol is transformed into higher alcohols; (2) a hydrogenolysis step wherein at least a portion of the byproducts of the Guerbet reaction are transformed into their parent alcohols; and (3) an etherification step in which at least a portion of the higher alcohols are transformed into ethers.

The hydrogenolysis reaction product comprises mainly higher alcohols and unconverted primary alcohols. The process may further comprise recycling the unconverted primary alcohol and butanol after the hydrogenolysis step to the Guerbet reaction.

In the etherification process and in some embodiments of the Guerbet process, some olefin byproducts are obtained. The process may further comprise an oligomerization step to oligomerize at least a portion of the olefin byproducts to increase their average molecular weight such that they reach a similar size to the olefins typically found in diesel.

The process disclosed herein results in a higher yield of large ethers, a direct consequence of the use of the recycle stream containing butanol in the Guerbet reaction. Additionally, the use of hydrogenolysis immediately after the Guerbet reaction simplifies the required separations significantly.

Guerbet Coupling

The process according to the present disclosure comprises a Guerbet coupling step to react primary alcohols to obtain a product comprising higher alcohols. Specifically, a feed comprising primary alcohols is contacted with a first catalyst in a first reactor under conditions effective to produce an effluent comprising higher alcohols.

The primary alcohol feedstock preferably comprises one or more C2 to C5 alcohols (i.e., methanol to pentanol), and most preferably comprises ethanol. One of the major products of Guerbet coupling of ethanol is butanol. When at least a portion of that butanol is recycled after the hydrogenolysis step to the Guerbet reaction, the primary alcohol feedstock would comprise ethanol and butanol. The generally accepted mechanism for the Guerbet coupling reaction (with ethanol as the reactant) is:

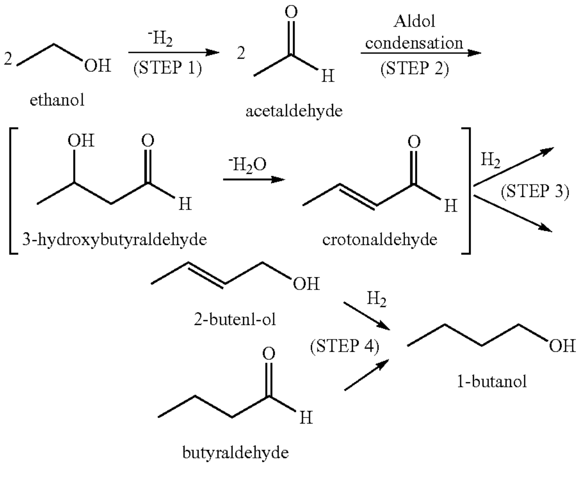

ethanol
acetaldehyde
3-hydroxybutyraldehyde
crotonaldehyde
2-butenl-ol
1-butanol
butyraldehyde The higher alcohols produced from the Guerbet coupling comprise one or more C4+ alcohols. Preferably, the higher alcohols comprise C6+ alcohols.

The products of the Guerbet coupling further comprise esters, aldehydes, and ketones as byproducts.

The Guerbet coupling reaction is preferably performed at a temperature from about 250° C. to about 370° C., preferably from about 280° C. to about 350° C., and more preferably still from about 300° C. to about 340° C.

Any catalyst now known or developed in the future that catalyzes Guerbet coupling reactions may be used. The Guerbet coupling catalyst is preferably a heterogeneous catalyst comprising one or more Group A oxides, the Group A oxides being oxides of Mg, Ca, Zn, Mn, Sr, Si, and/or Zr; or one or more Group B oxides, the Group B oxides being oxides of Al, La, Ga, Ce, Fe, Sc, Cr, P and/or V; and combinations of both Group A and Group B oxides. The Guerbet coupling catalyst may optionally comprise or more of Cu, Ni, Pt, Pd, Rh, Co, Cs, and Rb.

The Guerbet coupling catalyst may also be a heterogeneous catalyst comprising one or more oxides of Mg, Ca, Zn, Sr, Al and Ce. In some embodiments, the Guerbet coupling catalyst comprises an oxide of Mg, Ca, Zn, Sr, Al or Ce.

Another type of Guerbet coupling catalyst may be a three-part heterogeneous catalyst comprising one or more oxides of Mg, Ca and Zn, one or more oxides of Al, La, Ga, Ce, Fe and Cr, and one or more of Cu, Ni, Pt, Pd, Rh and Co.

Additionally, the Guerbet coupling catalyst may be a heterogeneous catalyst comprising one or more oxides of Mg, Ca and Sr, one or more of P and V, and, optionally, one or more of Cu, Ni, Pt, Pd, Rh and Co.

The Guerbet coupling catalyst may be a heterogeneous catalyst comprising Al and Si metal oxides and one or more of Cs and Rb.

The weight percent of the one or more of Cu, Ni, Pt, Pd, Rh and Co in the Guerbet coupling catalyst may be up to about 10 wt. %, or from about 0.01 wt. % to about 9 wt. %, or from about 0.01 wt. % to about 8 wt. %, or from about 0.01 wt. % to about 7 wt. %, or from about 0.01 wt. % to about 6 wt. %, or from about 0.01 wt. % to about 5 wt. %, or from about 0.01 wt. % to about 4 wt. %, or from about 0.01 wt. % to about 3 wt. %, or from about 0.01 wt. % to about 2 wt. %, or from about 0.01 wt. % to about 1 wt. %, or from about 0.01 wt. % to about 0.5 wt. %, or from about 0.01 wt. % to about 0.4 wt. %, or from about 0.01 wt. % to about 0.3 wt. %, or from about 0.01 wt. % to about 0.2 wt. %, or from about 0.01 wt. % to about 0.1 wt. %, based on the total weight of the catalyst.

In some versions of the method, the Guerbet coupling catalyst comprises Mg and Al oxides and Cu. The weight percent of Cu is preferably about 0.05 wt. % to about 1.0 wt. %, or 0.05 wt. % to 0.5 wt. %, or 0.05 wt. % to 0.2 wt. %, based on the total weight of the catalyst.

Generally, a Guerbet coupling catalyst having the desired activity can have a molar ratio of one or more of Mg, Ca, Zn, Mn, Sr, Si and Zr to one or more of Al, La, Ga, Ce, Fe, Sc, Cr, and V of about 10 to about 1, for example about 5 to about 1, about 4 to about 1, or about 3 to about 1. In some embodiments, the molar ratio of one or more of Mg, Ca, and Zn to one or more of Al, La, and Ga, can be at least about 10, for example at least about 5, at least about 4, or at least about 3. Additionally, or alternately, the molar ratio of one or more of Mg, Ca, and Zn, to one or more of Al, La, and Ga can be about 10 or less, for example about 5 or less, about 4 or less, or about 3 or less.

In some preferred versions, the molar ratio of Mg to Al, can be at least about 5, for example at least about 4 or at least about 3. In such embodiments, the molar ratio of Mg to Al can optionally be about 5 or less, for example about 4 or less, or about 3 or less.

In other versions of the method, the Guerbet coupling catalyst may be reduced prior to use. The catalyst may be reduced by treating it with hydrogen at elevated temperature.

Typical temperatures may be in the range of from about 250° C. to about 450° C., or between about 300° C. and about 400° C.

Hydrogenolysis

After the Guerbet coupling, the resulting intermediate product mix is subjected to hydrogenolysis to transform at least a portion of the ester, aldehyde and ketone byproducts of the Guerbet reaction into their parent alcohols. Specifically, the effluent of the Guerbet reaction is contacted with hydrogen and a second catalyst in a second reactor under conditions effective to convert esters, aldehydes, and ketones into their parent alcohols.

The reaction is preferably performed at a temperature of about 200° C. Any suitable hydrogenolysis catalyst may be used. A host of them are known in the art. See, for example, Kieboom and van Randwijk, "Hydrogenation and hydrogenolysis in synthetic organic chemistry," © 1977: Springer Press, NY, NY; ISBN-13: 978-9029801010. Hydrogen is preferably provided in large excess to drive the hydrogenolysis as far toward completion as possible.

The second catalyst may be a heterogeneous catalyst comprising one or more metals selected from Cu, Ni, Rh, Ru, Ir, and Pd; and a support. The support includes, but not limited to ZrO, ZnO, C, and alumina.

In some versions of the method, the hydrogenolysis catalyst is a copper-based catalyst.

The effluent of the hydrogenolysis is then separated, fractionated, or partially enriched. This can be accomplished via a sequence of distillation columns and a molecular sieving unit. The resulting ethanol and butanol are recycled to the Guerbert reaction. The stream rich in higher alcohols is split into two fractions: a heavy product comprising C10+ alcohols directly used in the diesel product blend; and a lighter product comprising C4-C9 used as a feedstock in the etherification reaction.

Etherification

The process according to the present disclosure also comprises an etherification step to transform higher alcohols to ethers. Specifically, higher alcohols from the effluent of the hydrogenolysis step are contacted with an etherification catalyst in a third reactor under conditions effective to dehydrate the higher alcohols to ethers.

The reaction may be performed at a temperature from about 100° C. to about 180° C.

The etherification catalyst may be any catalyst, now known or developed in the future, that catalyzes the production of ethers from alcohols. Solid acid catalysts are preferred. Exemplary solid acid catalysts that can be used in the method comprise one or more of acidic resins, alumina, and aluminosilicates, heteropoly acids, tungsten and/or molybdenum functionalized oxides, and the like. For example, the Amberlyst®-brand resins are functionalized styrene-divinylbenzene copolymers with different surface properties and porosities. The functional group is generally of the sulfuric acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co. Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated. Where an acidic material is provided on a support, the support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ may also be used as solid acid catalysts.

The ethers produced in the reaction comprise one or more C4-C20 ethers.

In addition to the ethers obtained, the reaction also tends to yield olefins (typically C4 to C9 olefins). The olefins are mainly the result from the dehydration of β-branched alcohols in the reaction blend. The C4-C6 olefins may further go through an oligomerization step to oligomerize the olefins to higher olefins.

Oligomerization

The process also comprises an oligomerization step to oligomerize the lighter olefins produced in the etherification step to higher olefins. Specifically, the lighter olefins are contacted with an oligomerization catalyst in a fourth reactor under conditions effective to form higher olefins.

The oligomerization catalyst may comprise acidic sites, such as those catalysts listed above for the etherification reaction. In some versions of the method, the catalyst comprising acid sites further comprises a transition metal, for example cobalt or nickel.

Preferably, the higher olefins produced through oligomerization comprise C8-C16+ olefins.

EXAMPLES

Summary

A representative schematic showing the method disclosed herein is shown in FIG. 1. The schematic shows the conversion of ethanol into diesel. The ethanol feedstock is for illustration only; any primary alcohol may be used in the feedstock. As shown in the figure, ethanol is used as the feedstock for a Guerbet reaction, in which higher alcohols (C4+) are obtained as the main product along with esters, aldehydes and ketones as byproducts. Additionally, wastewater is obtained as a result of the alcohol condensation reaction. The outlet from the Guerbet coupling reaction is used as the feedstock of a hydrogenolysis reaction in which esters, aldehydes, and ketones are transformed into their parent alcohols. The hydrogenolysis reaction product comprises mainly higher alcohols, and unreacted ethanol. In this Example a recycling strategy has been implemented in which the unconverted ethanol and a significant fraction of the butanol produced in the Guerbet reactions are sent back to the Guerbet reactor. This recycle loop leads to an operation in which ethanol and butanol are co-fed to the Guerbet reactor. The presence of butanol in the feed to the Guerbet reaction yields coupled products of increased molecular mass (as compared to using solely ethanol in the feed). The partial recycling of butanol is also helpful to reduce butanol content in the etherification step. The fraction of unrecycled butanol, along with the C6+ alcohols produced in the Guerbet coupling are split into two fractions, C4-C8 alcohols are fed to an etherification reaction in which ethers with 8-16 carbons are produced. Larger alcohols (C10+) can be used directly as part of the diesel blend. In the etherification process some olefin byproducts (mainly C4-C8) are obtained. These components are oligomerized to increase their average molecular weight such that they reach a similar size to the olefins typically found in diesel. Energy rich purge streams obtained in the hydrogenolysis and Guerbet coupling section of the plant are used to partially offset the energy needs of the refinery.

Producing Higher Alcohols From Ethanol

Guerbet Coupling:

For the Guerbet coupling reaction, a $Cu/Mg_3ALO$ catalyst was used that was recently developed. (See Cuello-Penaloza et al., "Reaction chemistry of ethanol oligomerization to distillate-range molecules using low loading Cu/MgxAlOy catalysts," *Appl Catal B,* 5 Dec. 2022, 318, 121821. This catalyst has important advantages in comparison with other heterogenous catalysts used for Guerbet coupling: it is low cost, it produces a larger fraction of C6+ alcohols, and it is stable (it has been evaluated for more than 100 hours on stream). Guerbet coupling tests with a cofeed of ethanol–butanol 70-30% mol were performed to study the feasibility of recycling ethanol and butanol into the Guerbet coupling reactor. Catalytic tests were conducted at three different space velocities WHSV=1.33, 6.5 and 26.2 $g_{ethanol}\,g_{cat}^{-1}\,h^{-1}$ (~70%, 50% and 30% ethanol conversion, respectively). Control experiments with pure ethanol feed were also performed at the same WHSV and reaction conditions.

Figure 2A:
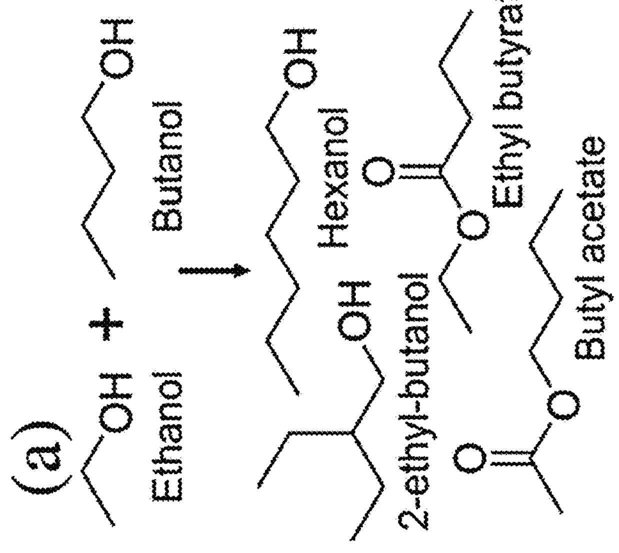
FIG. 2A. Conversion of ethanol and butanol into C6 alcohols and esters. Ratio of mole flow of alcohols in cofeed strategy/alcohols in control experiments, normalized by unit of time and mass of catalyst.

The motivation for recycling butanol into the Guerbet coupling reactor is to promote the rate of hexanol production by facilitating the overall reaction ethanol+butanol→hexanol+$H_2O$. Nevertheless, coupling between ethanol and butanol yields other compounds like 2-ethyl-butanol, which occurs when ethanol acts as an electrophile in the reaction. Moreover, for catalysts containing transition metals, other functionalities like esters are synthesized in the reaction pool. In this respect, the reaction between ethanol and butanol leads also to the production of butyl acetate and ethyl butyrate as presented in FIG. 2A. The product mix becomes even more complex because alcohols are allowed to react with themselves. For example, two ethanol molecules produce butanol or ethyl acetate and two butanol molecules can produce 2-ethyl-hexanol or butyl butyrate.

Figure 2B:
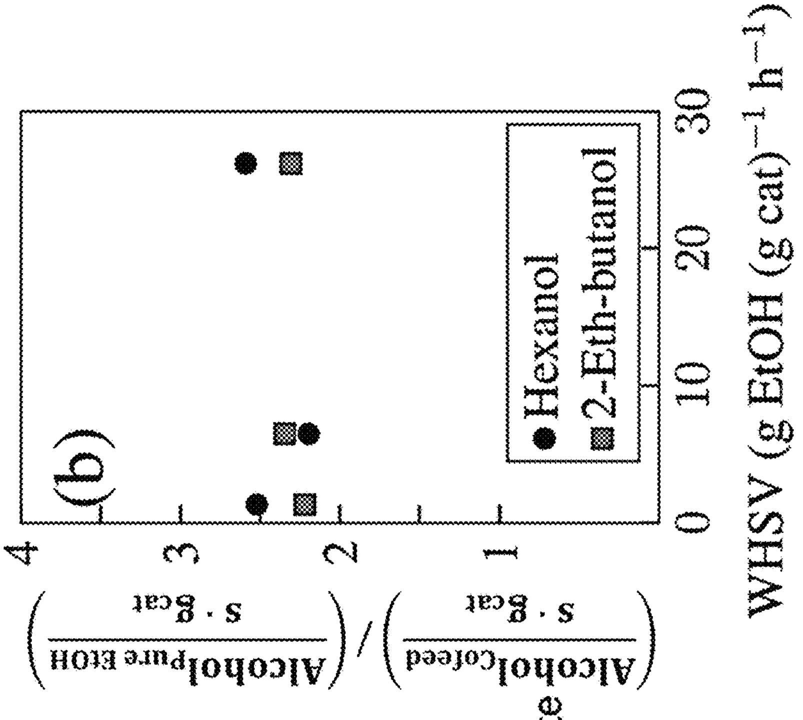
FIG. 2B Hexanol and 2-ethyl-butanol, and FIG. 2C. Octanol and 2-ethyl-hexanol. T=325° C., Ptot=300 psig, (Ethanol+Butanol):H2=4:1, 100-300 mg 0.1% Cu/Mg3AlO.
Figure 2C:
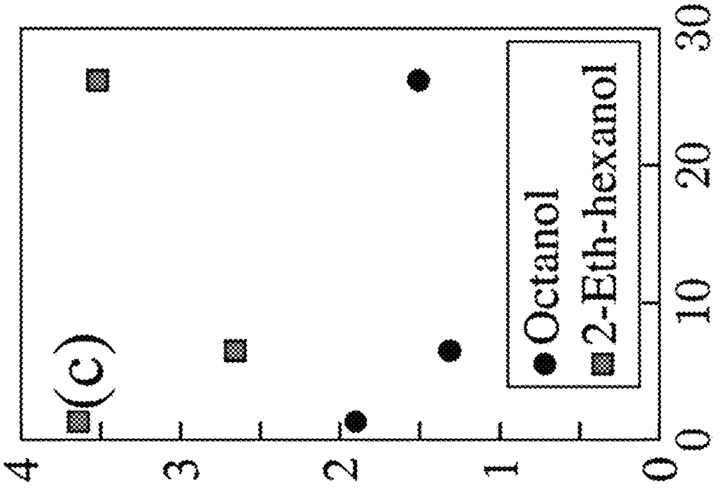
Figures 3A, 3B:
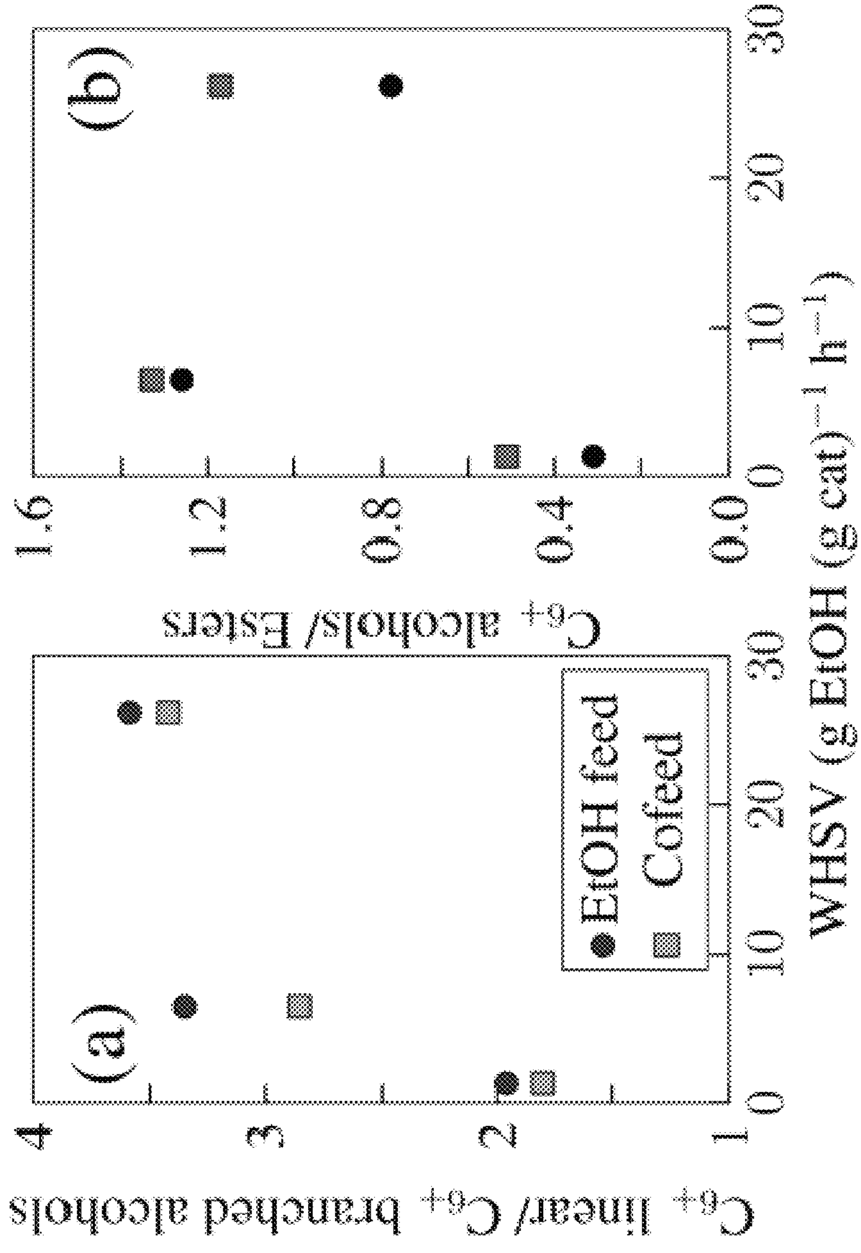
FIG. 3A. C6+ Linear to branched alcohols ratio and FIG. 3B C6+ alcohols to ester ratio when cofeeding Ethanol (70% mol)/Butanol (30%) (blue circles) accompanied with control experiments with pure ethanol feed (yellow circles). T=325° C., Ptot=300 psig, Ethanol+Butanol:H2=4:1, 100-300 mg 0.1% Cu/Mg3AlO.

Comparison of mol production of linear and branched alcohols between cofeed and control experiments is presented in FIGS. 2B-C. The data indicates that cofeeding alcohols boosts the formation of hexanol and 2-ethyl-butanol by a factor of 2.2 (FIG. 2B). This suggests that butanol presence in the feed does not change the nucleophilic/electrophilic role of ethanol in the reaction. Similarly, FIG. 2C shows that the production of C8 alcohols is enhanced by the cofeed of butanol to the reactor, with the caveat that the formation of the branched alcohol is more accelerated than the formation of octanol. FIG. 3A shows that overall linear alcohols are formed preferentially, demonstrating that a cofeed strategy is selective to produce the most relevant diesel fuel precursors.

Figure 4A:
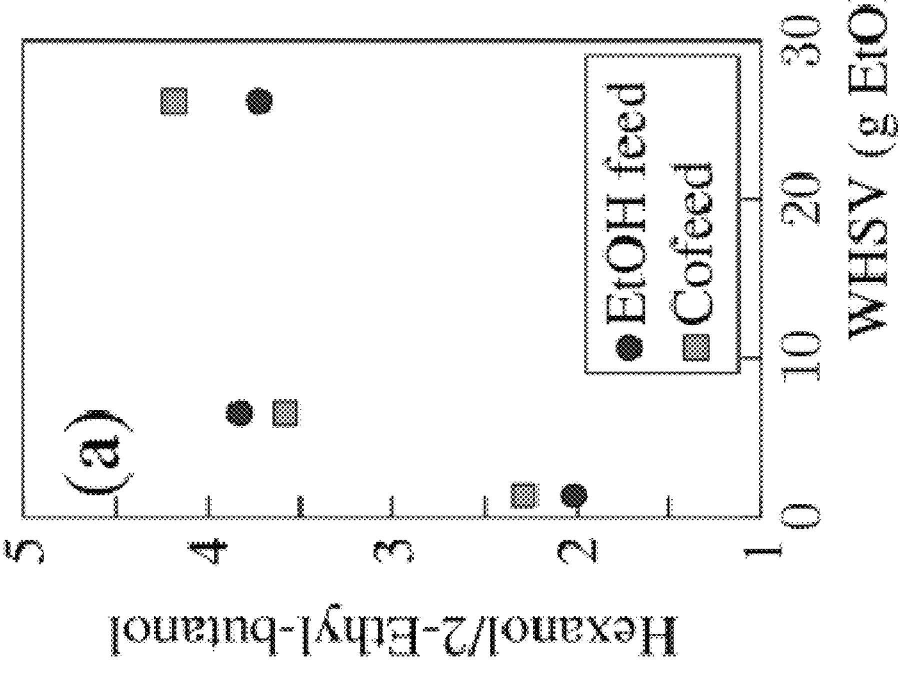
FIG. 4A Mol ratio of Hexanol to 2-Ethyl-butanol FIG. 4B Mol ratio of Octanol to 2-Ethyl-hexanol when cofeeding Ethanol (70% mol)/Butanol (30%) accompanied with control experiments with pure ethanol feed. T=325° C., Ptot=300 psig, Ethanol+Butanol:H2=4:1, 100-300 mg 0.1% Cu/Mg3AlO.
Figure 4B:
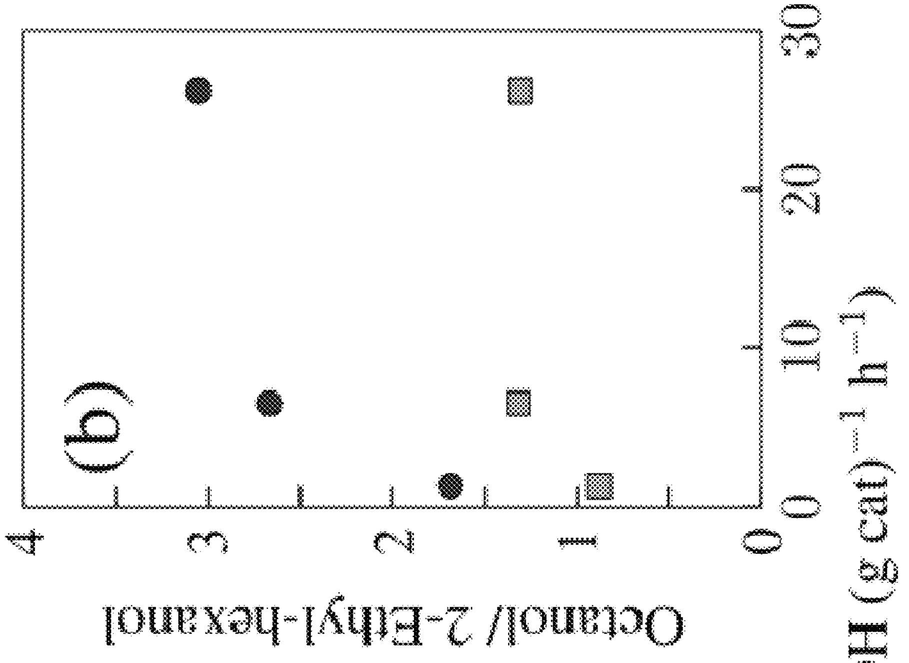

Previous etherification studies[5,24] over acid catalysts have demonstrated that linear alcohols undergo preferentially bimolecular dehydrations to produce ethers, whereas branched alcohols are more prone to form olefines through monomolecular dehydration. See Restrepo-Florez 2023 and Kim et al. 2010 *Jpn. J. Appl. Phys.* 49 05EA04; DOI: 10.1143/JJAP.49.05EA04. Therefore, tracking the ratio of linear to branched alcohols is important. FIGS. 4A-4B show this ratio for C6 and C8 alcohols, respectively. Our results indicate the catalyst is selective to form linear alcohols (values >1). For C6 alcohols, the ratio of hexanol to 2-ethyl-butanol is slightly higher in the cofeed experiments than in the control, indicating that cofeeding butanol facilitates the production of hexanol more than its branched counterpart. On average, the outlet hexanol molar flowrate is 3.4 and 3.2 higher than the mole flow of 2-ethyl-butanol for the cofeed and pure ethanol feed experiments, respectively. For C8 alcohols, a more noticeable difference is observed. FIG. 4B shows that cofeeding ethanol and butanol produces more 2-ethyl-hexanol in comparison with the control experiment. For reference, in the co-feed case the Octanol/2-ethyl-hexanol ratio is close to one; in contrast, in the control experiments, it ranges between ~1.5-3 depending on the WHSV. This increase in relative concentration of 2-ethyl-hexanol in the cofeed experiments can be explained by considering that octanol is formed only from the coupling of ethanol and hexanol, with the former acting as nucleophile and the latter as electrophile. In contrast, 2-ethyl-hexanol is produced either when hexanol is the nucleophile and ethanol the electrophile or by coupling of two butanol molecules. Thus, cofeeding butanol enhances butanol self-condensation to form 2-ethyl-hexanol.

Figures 5A, 5B, 5C:
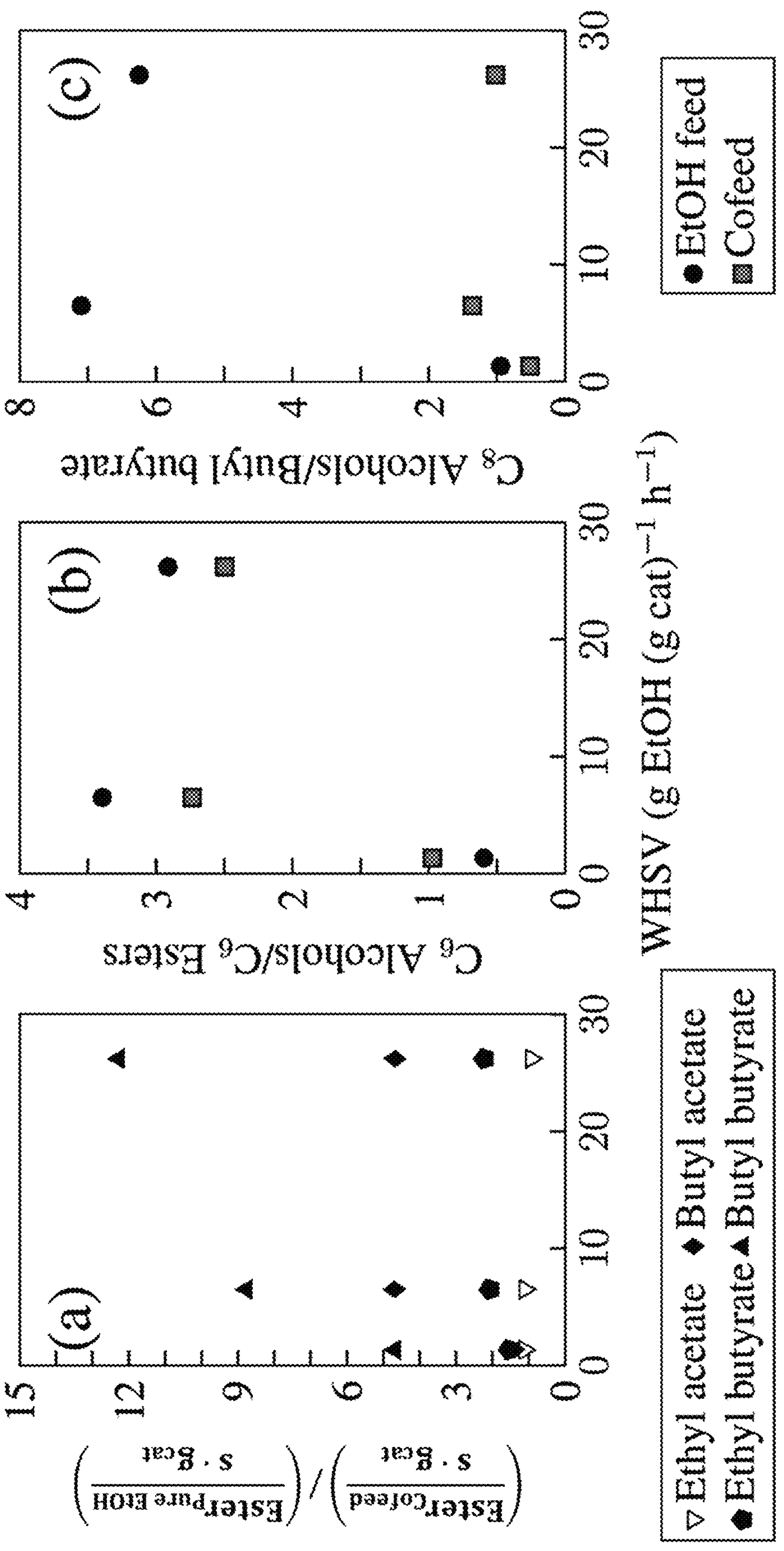
FIG. 5A Mol flow of esters in cofeed strategy/esters in control experiments, FIG. 5B mol ratio of C6 alcohols to C6 esters, and FIG. 5C mol ratio of C8 alcohols to butyl butyrate as a function of WHSV for cofeed strategy and control experiments.

FIG. 5A shows the production of esters from ethanol/butanol coupling. Production of ethyl acetate remained unchanged in cofeed and control experiments. In contrast, production of other esters like ethyl butyrate, butyl acetate, and butyl butyrate is enhanced. The data shows that butyl acetate is produced preferentially over ethyl butyrate, which is due to the large excess of ethanol (70% mol in feed) that induces formation of acetaldehyde and subsequently dehydrogenative coupling between acetaldehyde and butanol. The presence of butanol in cofeed experiments leads to a higher production of butyl butyrate compared to the control experiments. The overall selectivity of C6+ alcohols with respect to esters is presented in FIG. 3B. This figure suggests that the Guerbet coupling stage will benefit from a cofeed strategy since the ratio C6+ alcohols to esters improves. We note that the production of long chain alcohols competes strongly with ester formation, given that the values in FIG. 3B are around 1.

The carbon yield (equation (1)) to diesel fuel precursors (alcohols, aldehydes, ester, ethers, and ketones) is presented in Table 2. For simplicity, the information has been condensed into categories based on functional groups. In equation (1), n_(C,in) refers to the total carbon flow rate entering the Guerbet reactor, while n_(C,i,out) refers to the carbon flowrate in the outlet of the reactor specifically for the compound i.

$$Y_i = \frac{n_{C,i,out}}{n_{C,in}} \quad (1)$$

TABLE 2

Carbon yields of main compound categories for cofeed and control experiments at ethanol contact times. Conditions: 325° C., 300 psig, P(EtOH + ButOH):PH2 = 4.

| Experiment | Cofeed 1 | Control 1 | Cofeed 2 | Control 2 | Cofeed 3 | Control 3 |
|---|---|---|---|---|---|---|
| WHSV ($h^{-1}$) | 26.27 | 26.27 | 6.53 | 6.53 | 1.33 | 1.33 |
| C balance (%) | 99.7 | 100.0 | 94.5 | 96.5 | 95.8 | 91.1 |
| EtOH conversion (%) | 26.57 | 33.16 | 41.75 | 41.87 | 66.04 | 73.88 |
| Diesel fuel precursor yield (%) | 7.76 | 6.18 | 13.41 | 10.68 | 28.90 | 23.54 |
| C6+ alcohol (%) | 4.04 | 3.08 | 6.67 | 5.77 | 7.36 | 5.05 |
| C6+ aldehyde (%) | 0.90 | 0.83 | 1.26 | 1.26 | 3.17 | 2.80 |
| C6+ ester (%) | 2.28 | 1.18 | 3.67 | 1.90 | 11.43 | 10.43 |
| C4+ ketones (%) | 0.47 | 0.65 | 1.46 | 0.75 | 6.86 | 4.92 |

As presented in Table 2, the yield to diesel fuel precursors increases in our cofeed strategy in comparison to the control experiments. Percentage increments were between 1.58 to 5.36. The main contributors for such indicator are alcohols and esters, which show an average increment of ~1 percentage point each one.

Hydrogenolysis:

The molar composition of the stream fed to the etherification area is a complex mixture of alcohols and esters (ester fraction can be as high as 7.5%[5]). Considering that esters significantly affect the catalytic performance of the etherification reactors, a hydrogenolysis stage is used in which esters, aldehydes, and ketones react in the presence of hydrogen to produce their parent alcohols. In this Example, the hydrogenolysis reactions employed a $Cu/ZrO_2$ catalyst previously reported. See Schittkowski et al. *J Catal,* 2017, 352, 120-129 and Zhang et al., *Catal Today,* 2021, 374, 53-60. The reactions were carried out using a representative blend of alcohol and ester. In this blend, butanol was selected as the representative alcohol due to its relative abundance in the feedstock and hexyl acetate was selected as the representative ester because it contains two alkyl chains that are not butyl. In this way, transesterification reactions were easier to track without isotopic labelling of reactants.

Figure 6C:
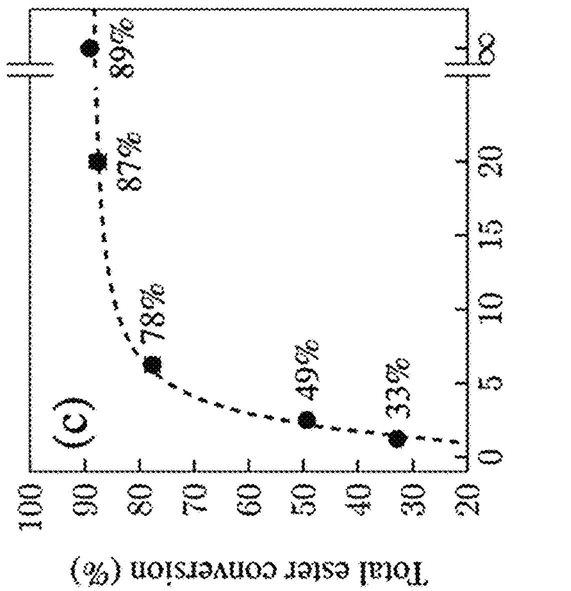
FIGS. 6A-B mole concentration (M) in the liquid product at the outlet of the hydrogenolysis reactor for the reactants and most abundant products and FIG. 6C total ester conversion as a function of the inverse of the WHSV for a blend of 5% hexyl acetate and 95% butanol (mol/mol), T=200° C., $P_{tot}$=420 psig, hexyl acetate:$H_2$=1:480, 100-300 mg of 10% wt. Cu/$ZrO_2$. Data at 1/WHSV=∞ corresponds to the equilibrium concentrations from Aspen Plus.
Figure 6B:
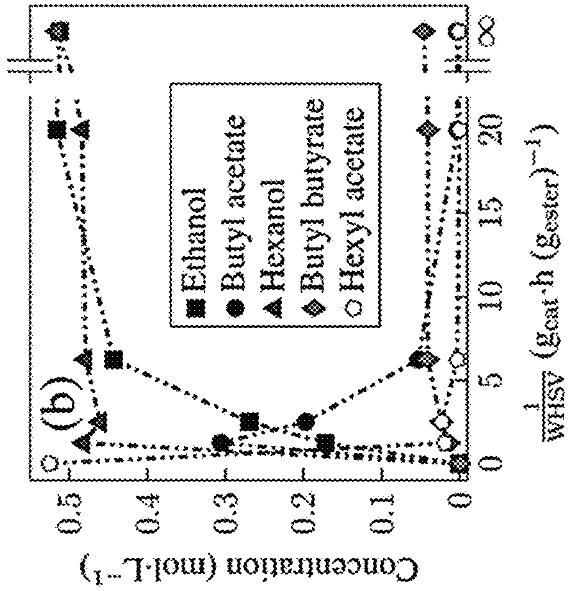
Figure 6A:
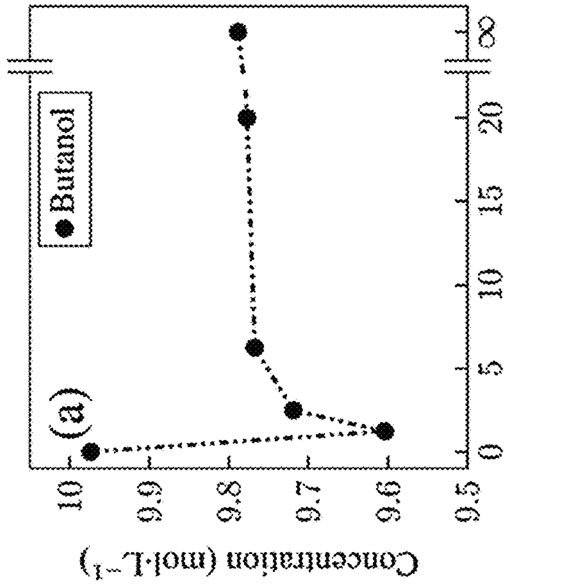

Experimental results for the catalytic reduction of esters through hydrogenolysis are shown in FIG. 6 for the hexyl acetate–butanol model feed. Concentrations presented in the panels A and B refer to the liquid phase after condensation of the effluents leaving the hydrogenolysis reactor. As observed in FIG. 6A, butanol concentration presents a rapid decrease from 9.97 M to 9.6M (1/WHSV=1.23). Interestingly, butyl acetate exhibits the opposite trend (see FIG. 6B) by going from 0 to 0.3M in the same contact time frame. In addition, hexanol concentration is observed to grow rapidly reaching values close to those of hexyl acetate at contact time zero, while ethanol rises more modestly as contact time increases, reaching similar concentrations to hexanol at high contact times (~20 h). The observed trend is an indication for a two-stage process, where initially hexyl acetate undergoes a transesterification reaction ruled by hexyl acetate+butanol→butyl acetate+hexanol, and then butyl acetate undergoes the hydrogenolysis, releasing the ethanol and butanol moiety, explaining the concentration rise of butanol and ethanol at 1/WHSV>1.23 h. We believe that butyl acetate is the main species that suffers the hydrogenolysis reaction, however we do not preclude that a fraction of the hexyl acetate fed to the system can also suffer catalytic reduction. Interestingly, butyl acetate arises as the predominant ester between 1/WHSV=1.33 and 6.25 h, while butyl butyrate concentration becomes more important at contact times higher than 6.25 h.

Based on the species identified experimentally and considering the poor ability of copper to cleave C—C bonds, we postulate that the system can be accurately described by reactions (R1) and (R2). (R1) is hydrogenolysis of the ester. (R2) involves hydrogenation of the aldehyde.

(R1)

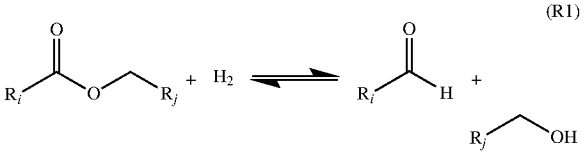

(R2)

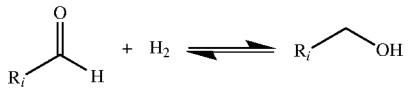

We have then performed thermodynamic equilibrium calculations at the reaction conditions in Aspen Plus V12.1 by implementing a linearly independent set of equilibrium reactions derived from the systematic combination of ethyl, butyl, and hexyl chains in reactions (R1) and (R2). Thermodynamic equilibrium calculations represent the limit case at which WHSV=0 h-1. For comparison purposes, the results of the thermodynamic calculations are depicted in FIGS. 6A and 6B at 1/WHSV=∞. FIGS. 6A and 6B show that extrapolation of the experimental molar concentration of all the species identified in the outlet of the hydrogenation reactor agree with the thermodynamic equilibrium calculations performed in Aspen.

Figure 7A:
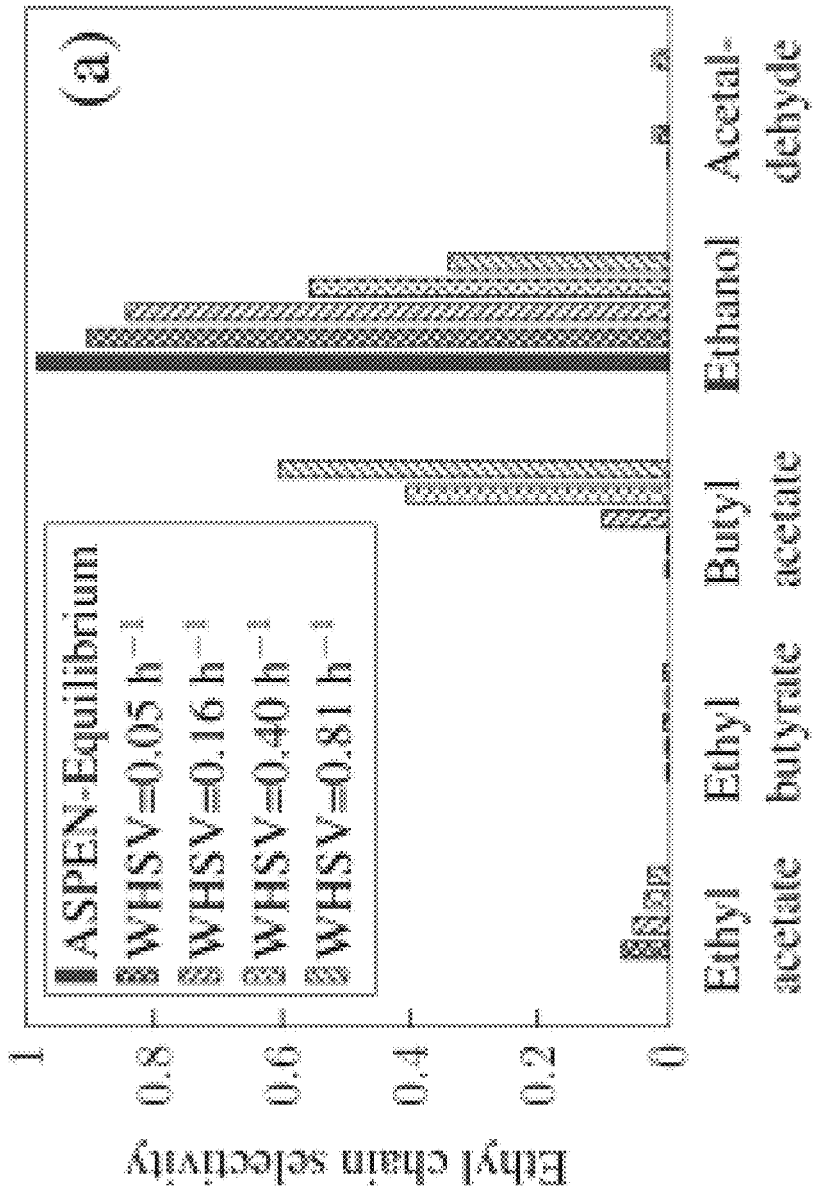
FIG. 7A. Alkyl chains selectivity at various WHSV for a blend of 5% hexyl acetate and 95% butanol, T=200° C., Ptot=420 psig, hexyl acetate:H2=1:480, 100-300 mg 10% wt. Cu/ZrO2. The butyl hexanoate marked with *in FIG. 7B

In reactions (R1) and (R2) it is observed that bond transformations come from C—O cleavage and hydrogenation of C═O, which implies no change of identity in alkyl chains $R_i$ and $R_j$. In other words, the moles of each alkyl chain are conserved (alkyl chain balance is usually >95% for all our experiments). This fact allows us to easily identify the fate of each alkyl chain and represent our results in terms of alkyl chain selectivity as defined by the equation (2).

$$S_{j,k} = \frac{\mathrm{mol}(ac_j)_k^{outlet}}{\sum_i \mathrm{mol}(ac_j)_k^{outlet}} \qquad (2)$$

Where $S_{j,k}$ represents the selectivity of alkyl chain j to product k, and $(ac_j)_k$ the alkyl chain j in product k in the outlet of the reactor, with j={ethyl, butyl, hexyl}. In our case k adopts the name of those compounds identified in the reactor product and shown on the x-axis of FIG. 7A-C. As depicted in FIG. 7A, ethyl chains from hexyl acetate formed initially butyl acetate (due to hexyl acetate and butanol transesterification), and subsequently suffered the hydrogenolysis, which released the ethyl moieties to form ethanol.

Figure 7B:
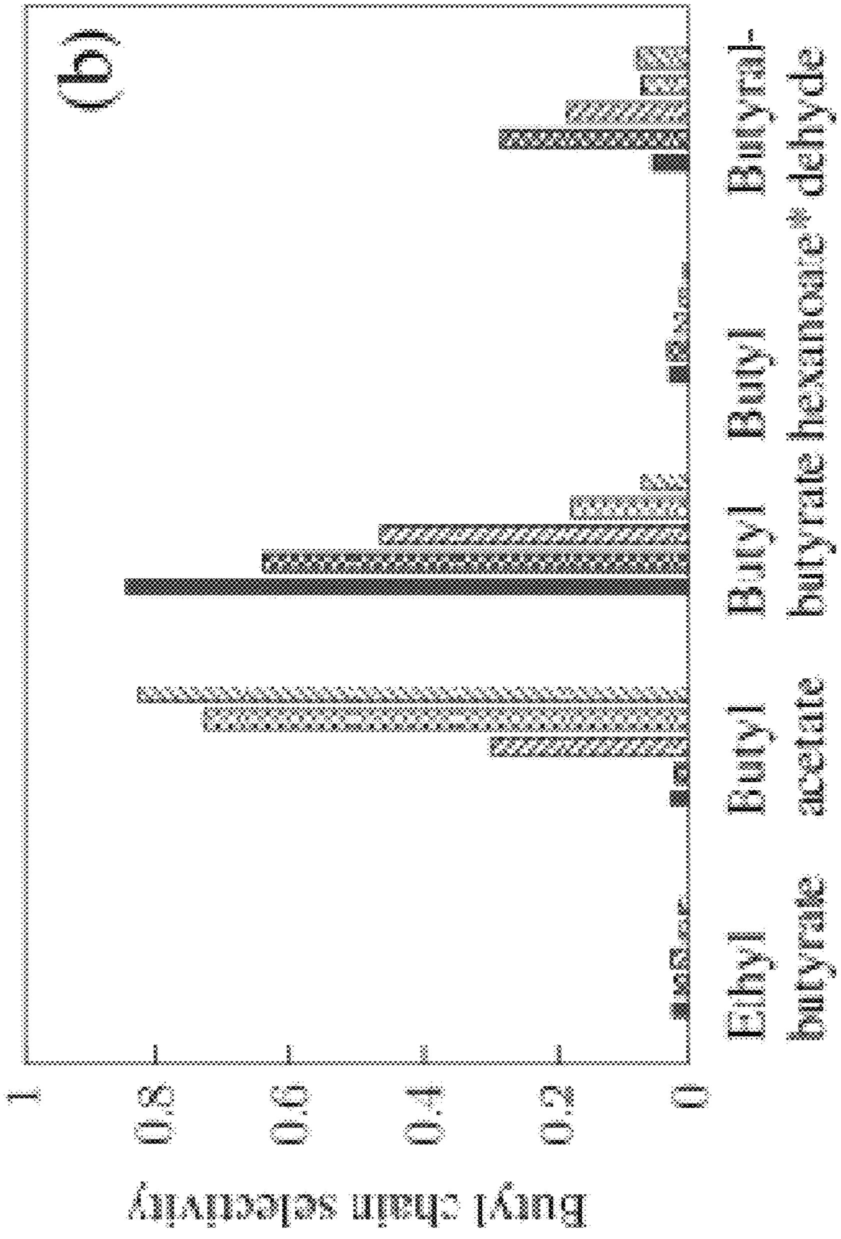
FIG. 7C represents the sum of butyl hexanoate and hexyl butanoate given that both esters had similar retention times in our analytics and peak deconvolution was not possible to differentiate both species.
Figure 7C:
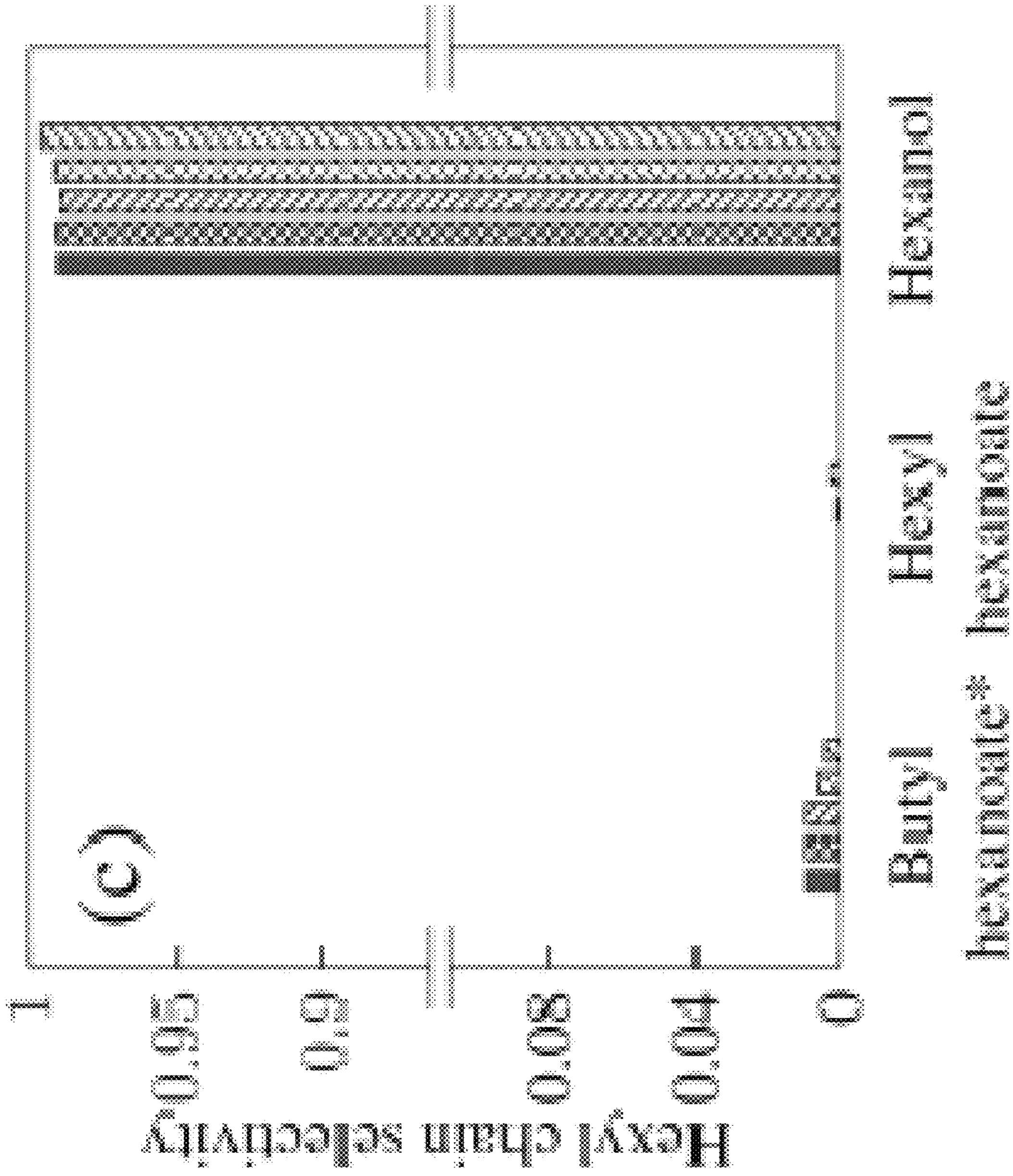

Other species containing ethyl chains like ethyl acetate, ethyl butyrate and acetaldehyde were detected as products with low preference for ethyl chains. FIG. 7B, shows the selectivity for butyl chains. The results point out that reacted butanol molecules formed preferentially butyl acetate, butyl butyrate and butyraldehyde. Finally, FIG. 7C presents the selectivity for the hexyl chains. The data indicates that hexyl chains were hydrogenated to form hexanol, while butyl hexanoate was identified with a hexyl selectivity lower than 2%. Once again, our experimental data was compared with thermodynamic equilibrium calculations, demonstrating that at low WHSV values the alkyl chains tend to follow the equilibrium distribution.

Figure 8:
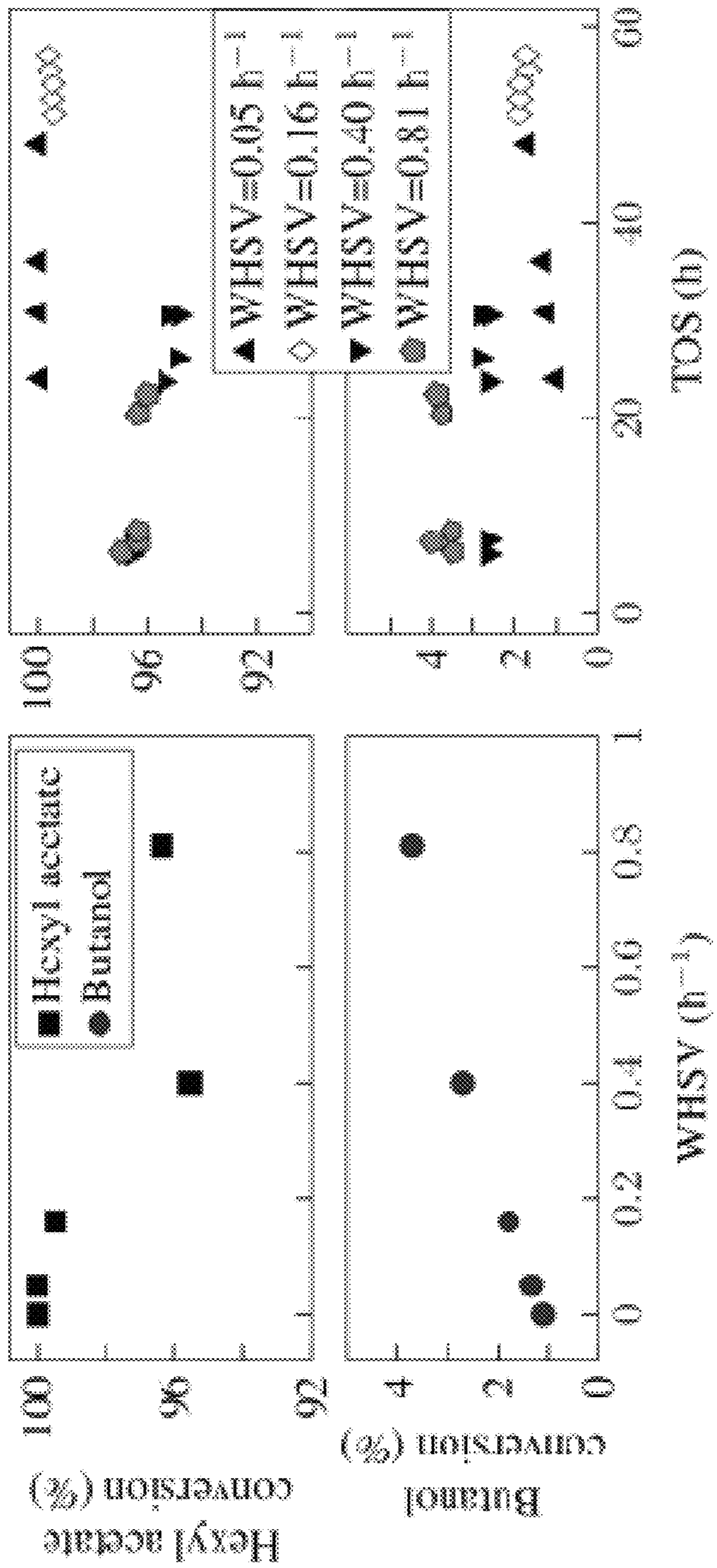
FIG. 8. Hexyl acetate and Butanol conversion as a function of WHSV (left) and TOS (h) (right).

Overall, the data presented in FIG. 6 shows that at high contact time (1/WHSV) the system converts most of the hexyl and acetate moieties into hexanol and ethanol, respectively. FIG. 8 shows that butanol conversion remains low (<4%), which indicates that the goal of performing the catalytic reduction of esters, while maintaining the butanol unreacted was satisfactorily achieved. FIG. 8 also depicts the stability of the Cu/ZrO2 catalysts by tracking conversion of the reactants as a function of time on stream (TOS). Both for hexyl acetate and butanol the conversion remains unchanged up to 60 h. Deactivation of the catalyst in such a timeframe and conversion regime is then assumed as negligible, since carbon and mass balances lied typically between 93%-100%.

While it is known that esters have a negative effect on the etherification reaction, the role of each a particular ester on this reaction it is still unclear. Thus, to track the effectiveness of the hydrogenolysis reaction, we define a general function in terms of the amount of total esters conversion (Equation (3)). This function tracks the fraction of ester functionality removed without tracking particular esters. Experimental results are shown in FIG. 6C along with the equilibrium value obtained through simulations (1/WHSV=∞). The fraction of esters removed increases monotonically as the contact time increases, approaching the thermodynamic limit (89.1%) when 1/WHSV is 20 h (ester removal ~87.7%).

$$\text{Total ester conversion} = 1 - \frac{\sum_i ester_i^{outlet}}{\sum_i ester_i^{inlet}} \tag{3}$$

After proving the feasibility of the hydrogenolysis of esters diluted in an alcohol, an experiment with the complex etherification feedstock G-66 reported in Restrepo-Flórez et al. 2023 was run at a WHSV=0.07 $h^{-1}$. Herein, the complexity of the stream is reduced by neglecting compounds containing alkyl chains higher than eight carbons. Equilibrium calculations are also carried out for this system using Aspen plus®. Given the presence of secondary alcohols in the Guerbet coupling stream, new chemical reactions to define the equilibrium between secondary alcohols and their respective ketones were added (Equation (R3)).

(R3)

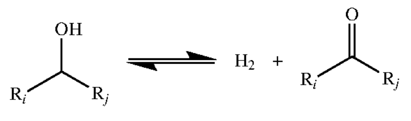

Figure 9:
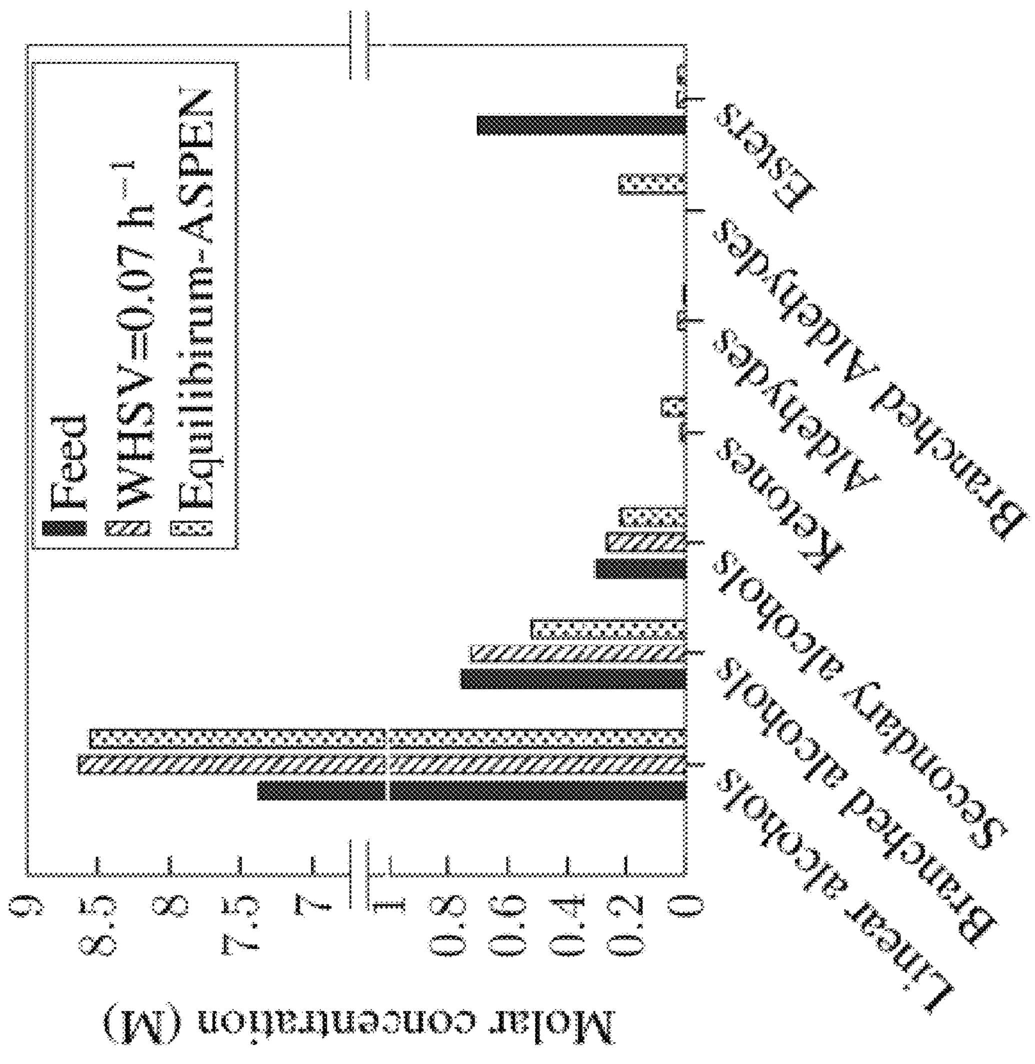
FIG. 9. Molar concentration in liquid phase for hydrogenation of a simulated Guerbet coupling stream. Experiment conducted at WHSV=0.07 h-1, T=200° C., Ptot=420 psig, Ester:H2=1:480, 500 mg 10% wt. Cu/ZrO2.

FIG. 9 presents the results of a catalytic esters reduction test using the simulated Guerbet coupling stream. The molar concentration distribution of the feed used in the experiment, the experimental liquid phase molar concentrations obtained in this study, and the equilibrium concentrations achieved in our simulations are shown in the figure. The results are calculated for the liquid phase after condensation of the products. The molar concentration of linear alcohols increased due to the hydrogenolysis of esters. Dehydrogenation of branched alcohols was not observed in our system, although thermodynamic equilibrium calculations suggest it should occur. We attribute this to slow dehydrogenation kinetics of such alcohols. On the contrary, secondary alcohols dehydrogenation to their respective ketones was observed. Overall, branched and secondary alcohols remained almost unchanged, while the main catalytic activity was due to hydrogenolysis of esters and hydrogenation of aldehydes. Our results suggest that butyl butyrate, hexyl butyrate, and butyl hexanoate became the predominant esters in the outlet stream of the reactor, owing to butanol and hexanol being the most abundant species in the feed. Overall, the ester mol fraction was reduced from 7.6% to 0.3%, the linear alcohols mol fraction increased from 80.81 to 89.1%, and the total alcohols mol composition increased from 92.3 to 99.3%. The total ester conversion calculated by Equation (3) is 96.0±0.2%, while the thermodynamic limit predicted in Aspen is 96.35%. This result is evidenced in FIG. 4, where esters molar concentration for our experiment and the thermodynamic equilibrium is virtually the same. A complete description of the molar concentration of each species identified in the outlet of the reactor can be found in table S6. These results highlight the feasibility of using hydrogenolysis to remove the esters produced in the Guerbet coupling reactor.

Figure 10:
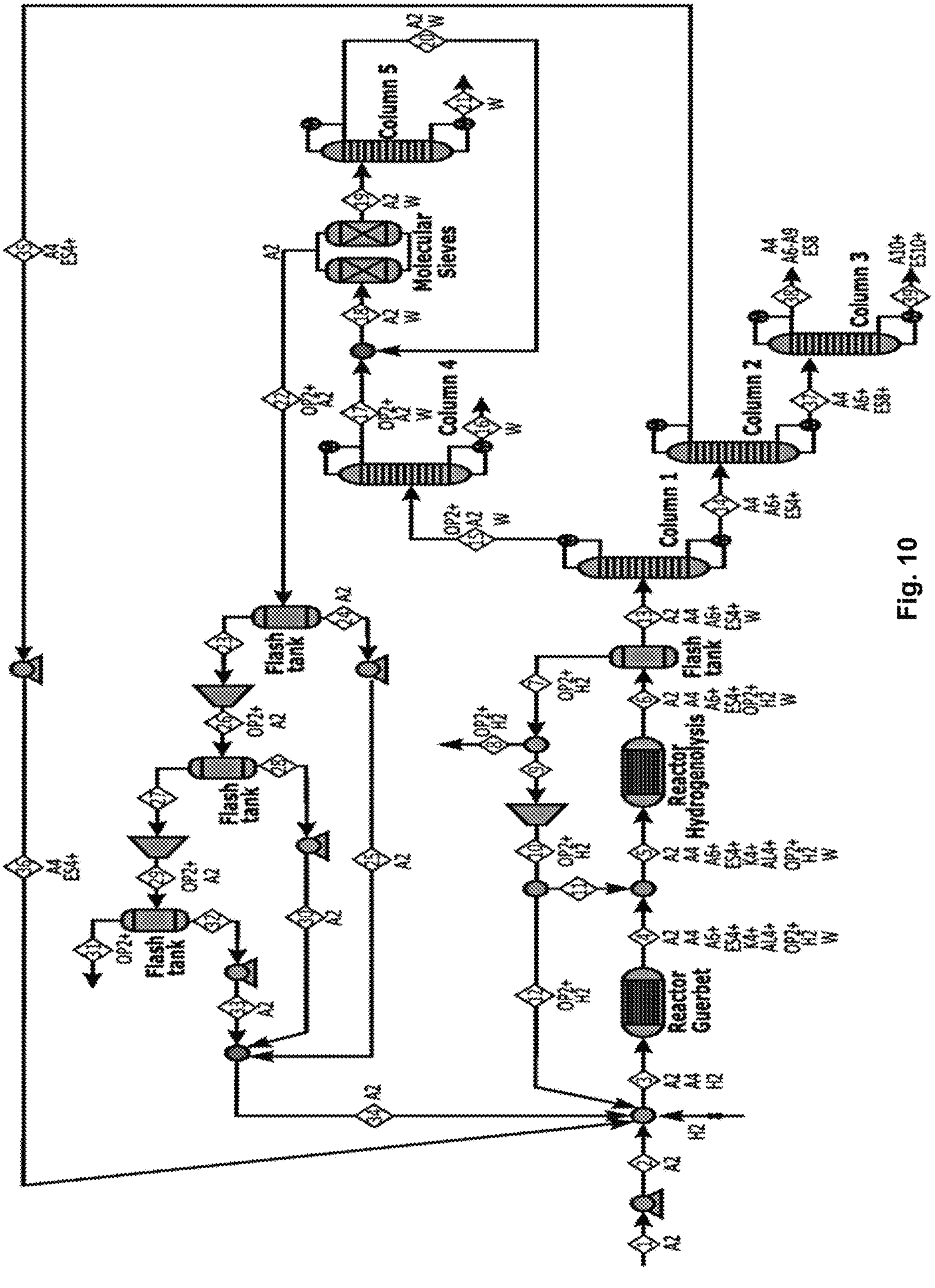
FIG. 10. Layout of the Guerbet and hydrogenolysis process. A: alcohols, ES: esters, K: ketones, AL: aldehydes, OP: olefins/paraffins, H: hydrogen, and W: water. The numerical characters indicate the carbon length.

Process Design:

Based on the results for Guerbet coupling with butanol recycle and the hydrogenation results (FIGS. 2 and 6), a process was designed for converting of ethanol into higher alcohols (FIG. 10). Specifically, the butanol recycle policy ensures an ethanol-to-butanol ratio in the reactor feed close to 70:30. Added to the coupling reaction is the hydrogenolysis step. Operational conditions (temperature, pressure, and hydrogen to alcohols ratio) were selected to ensure full conversion of ketones and aldehydes and 95% conversion of esters. The Guerbet coupling reactor was operated at 325° C. and 25 Bar with hydrogen as a carrier gas in a 1:4 ratio (hydrogen:ethanol+butanol). The hydrogenolysis reactor was operated at 200° C. and 25 Bar, with hydrogen in excess in a ratio of 400:1 (hydrogen:esters). Both reactors were designed to operate at a slightly higher pressure than the one reported here. This modification facilitates the subsequent separations. The products of the hydrogenolysis reactor were partially condensed in a flash tank, enabling the recycle of hydrogen. A sequence of distillation columns and a molecular sieving unit were used to facilitate the recycling of reactants (ethanol and butanol) (streams 34 and 36), the production of a two higher alcohol-rich streams (stream 37), and the removal of wastewater (streams 16 and 21). Column 3 splits stream 37 (which is rich in higher alcohols) into two fractions: a heavy product at the bottom containing alcohols with more than 10 carbons, and a light product, at the top, rich C4-C9 alcohols which is used as a feedstock in the etherification reaction. The heavy stream is blended directly into the diesel product.

Producing Ethers and Higher Olefins From Higher Alcohols

Figure 11:
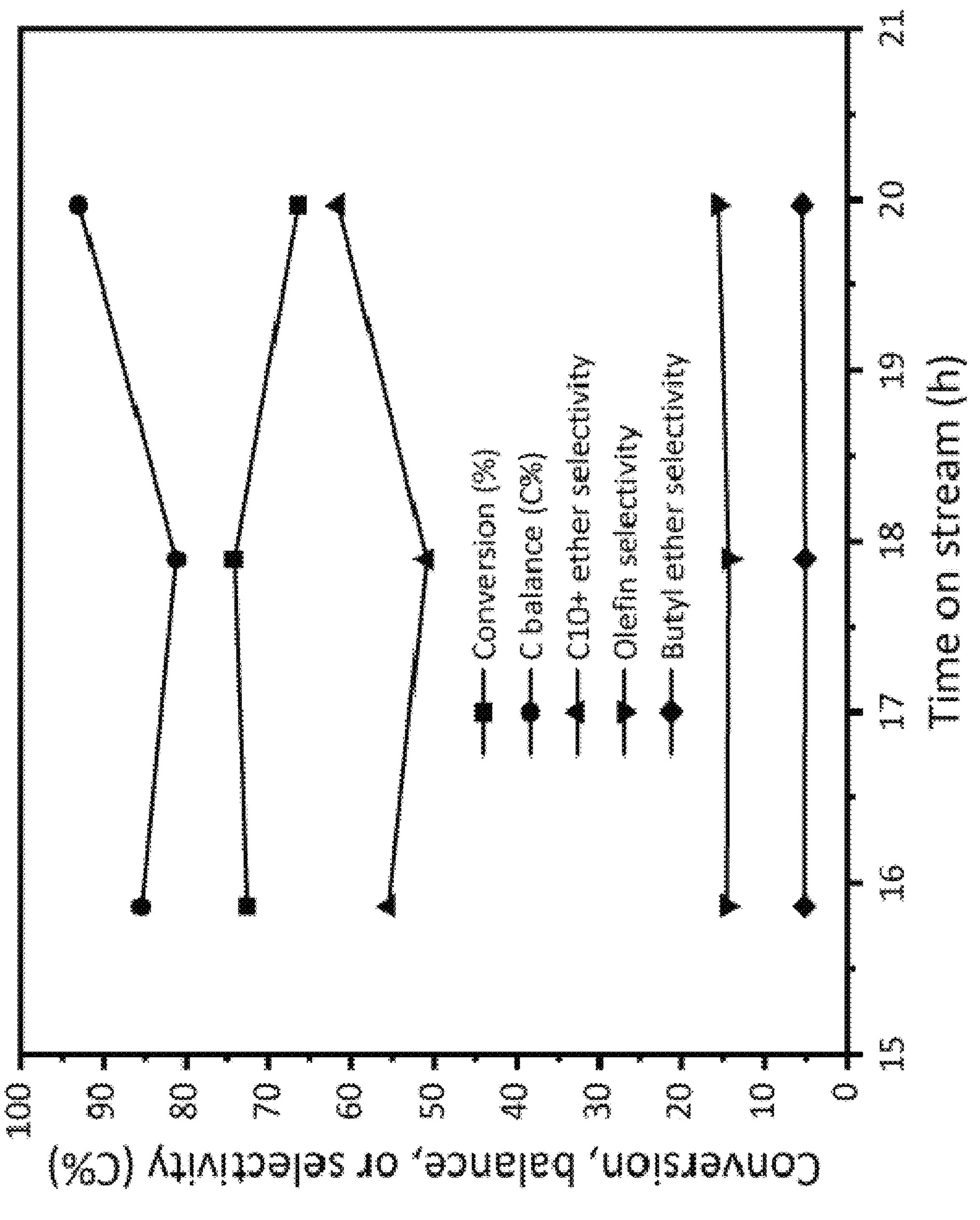
FIG. 11. TOS data of EtOH/oligomerization dehydration products. Reaction conditions: T=170° C., P=110 psig, feedstock flowrate=0.040 mL/min, Ar flowrate=10 mL/min, WHSV=1.085 h-1.

Etherification:

The alcohol rich stream produced in the Guerbet coupling area (stream 38) is used as a feedstock in an etherification reaction that uses HY zeolite as catalyst. For simplicity, in the etherification catalyst characterization experiments we have assumed complete removal of esters prior to entering the reactor. The addition of n-butanol in the ethanol oligomerization reactor leads to increased C6+ alcohol content, compared to when only ethanol is used. Here, the C6+ alcohol mol fraction is at ~60%, compared to our previous reported work, where we used a dehydration feed stream containing 30 mol % of C6+ alcohols. We also note that the addition of n-butanol in the oligomerization reactors leads to an increase in branched alcohols. This is expected, as alcohols larger than ethanol react as nucleophiles to produce larger branched products over alcohol coupling catalysts. Furthermore, the size of the secondary alcohols increases with the introduction of the n-butanol recycling stream, leading to an increase in the average size of the final olefin fuel precursors obtained from the dehydration reactor. A detailed breakdown of the selectivity obtained in this reaction (defined as the percentage of total mols of carbon contained in a product to the total mols of carbon converted) is shown in Table 3. Compared to our previous results (Restrepo-Florez et al 2023, Sustainable Energy and Fuels 7 (3), 693-707), we observe a reduction in the selectivity toward light ethers (e.g., n-butyl ether), showing a shift toward the production of larger distillate-range molecules. We note that while the C10+ ether selectivity slightly changes between previous results (~50% vs ~56% in this paper), there is also a noticeable change in the yield of C10+ ethers. In the current work, we increase the yield of distillate range molecules by reducing the butyl ether yield from 14% to 4%. This can be attributed to an increase in the fraction of C6+ alcohols in the feed stream. These results are an indication that the butanol recycling strategy implemented succeeded in reducing the amount of low molecular weight ethers formed. This demonstrates the possibility of using the butanol recycle fraction as a control variable to tune the molecular weight distribution of the products. In addition to the ethers obtained, we also observed a fraction of olefins (4 to 9 carbons). These olefins result from the dehydration of β-branched alcohols and secondary alcohols in the reaction blend. The catalyst used was tested by running a flow reactor for 21 h continuously. The results are shown in FIG. 11, where we show conversion, carbon balance, and products selectivity as a function of time on stream. These values remain relatively stable throughout the test.

Figure 12:
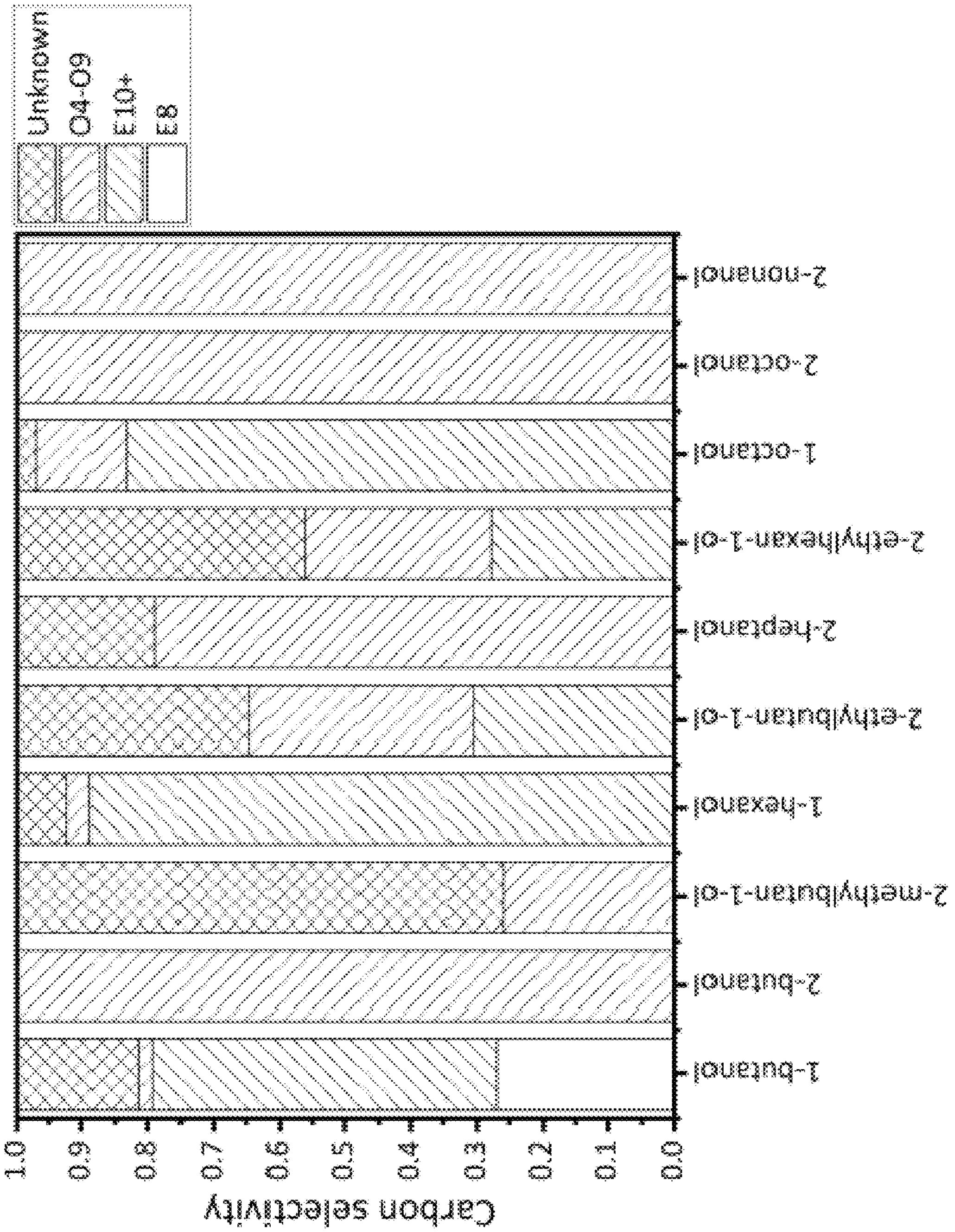
FIG. 12. Carbon selectivity for the etherification reaction when HY zeolite is used as catalyst. T=170.1° C., P=110 psig, feedstock flowrate=0.040 mL/min, Ar flowrate=10 mL/min, WHSV=1.085 h-1. Chemical species labeling in the legend: letter indicates species type, and number carbon length. O: olefins, E: Ethers.

Table 3 shows the conversion for each of the reactions that are happening in the dehydration step. Each alcohol in the feedstock can undergo different reactions leading to the formation of ethers or olefins. The observed ether and olefin carbon selectivity is shown in FIG. 12. The carbon selectivity $$\left(S_{i,j} = n_{i,j}^{out} / n_i^{Conv}\right)$$

is defined as the ratio between the mols of carbon in product j coming from alcohol $$i\left(n_{i,j}^{out}\right),$$

and the mols of alcohol i converted $$\left(n_i^{Conv}\right).$$

It is important to note that this selectivity is a function of the feed composition, since the presence of other alcohols determines the type of products that can be formed. We highlight that in the case of 1-butanol, around 50% of the carbon is converted into E10+ ethers (linear and branched).

TABLE 3

Carbon selectivity for etherification reaction using EtOH/recycled-ButOH oligomerization products (the feed stream is shown consist of the alcohols shown in table 3). Carbon not detected in the liquid or gas phase was assumed to go to coke products.

| Compound | Carbon # | Selectivity |
|---|---|---|
| Ethers | | |
| Butyl ether | 8 | 5.28 |
| Butyl ethyl-butane ether | 10 | 1.56 |
| $C_{10}$ linear ethers | 10 | 20.98 |
| Butyl ethyl-hexane ether | 12 | 0.85 |
| Hexyl ethyl-butane ether | 12 | 3.18 |
| $C_{12}$ linear ethers | 12 | 22.20 |
| Hexyl ethyl-hexane ether | 14 | 1.72 |
| Octyl ethyl-butane ether | 14 | 0.47 |
| $C_{14}$ linear ethers | 14 | 4.81 |
| $C_{16}$ linear ethers | 16 | 0.30 |
| Olefins | | |
| Butenes | 4 | 1.70 |
| $C_5$ olefins | 5 | 0.62 |
| $C_6$ olefins | 6 | 5.05 |
| Heptenes | 7 | 4.41 |
| $C_8$ olefins | 8 | 2.76 |
| Nonenes | 9 | 0.26 |
| Unknown products | — | 5.19 |
| Coke | — | 18.66 |

Figure 13:
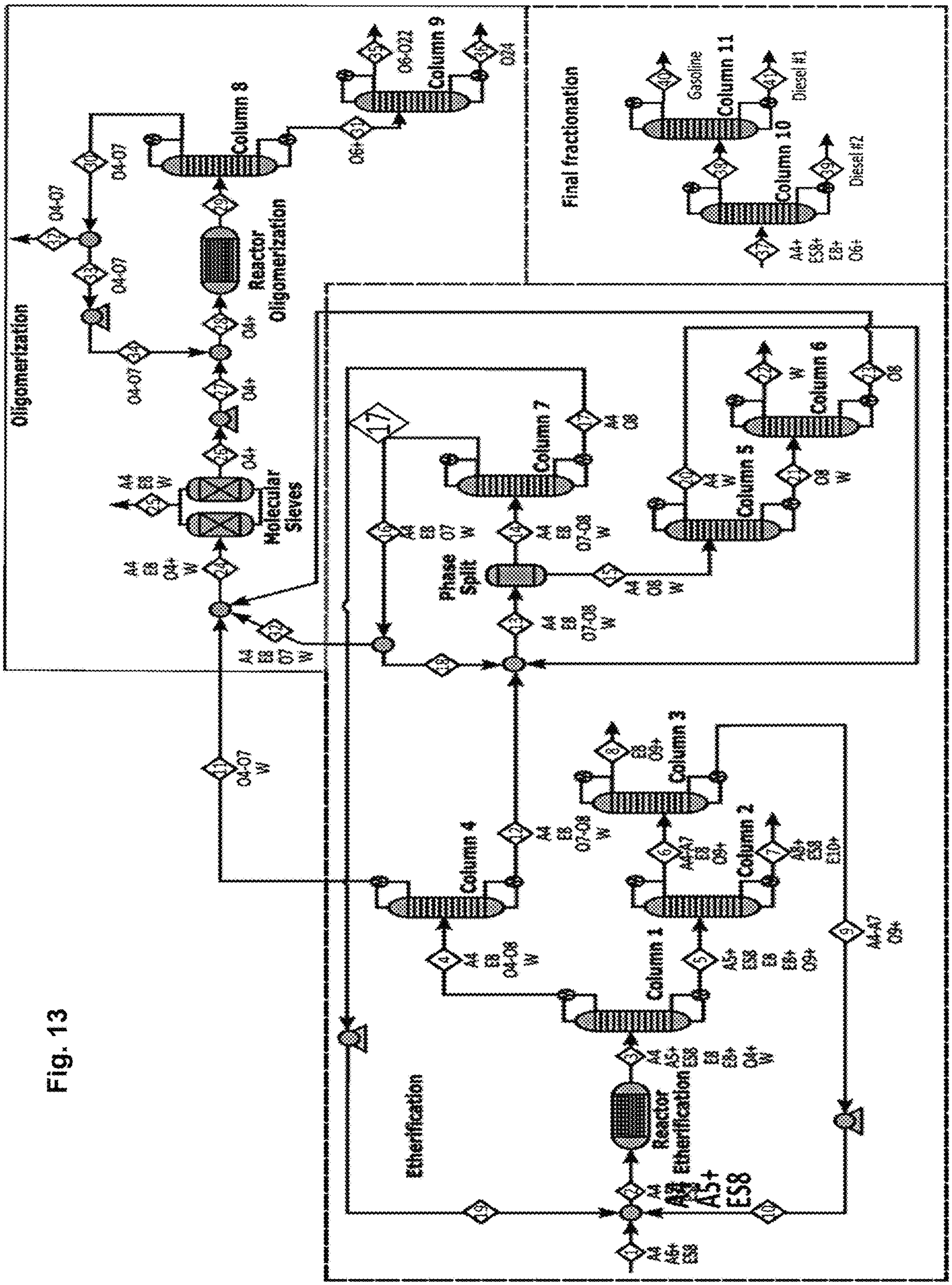
FIG. 13. Layout of the etherification, oligomerization, and final production fractionation sections. A: alcohols, ES: esters, K: ketones, AL: aldehydes, OP: olefins/paraffins, H: hydrogen, and W: water. The numerical characters indicate the carbon length.

Process Design:

A layout of the process is shown in FIG. 13. At a high level, a blend of alcohols produced by Guerbet coupling is used as a feedstock. This alcohol blend enters the etherification reactor. The products of this reaction are separated using a sequence of distillation operations (columns 1 to 4 in FIG. 13), along with a heteroazeotropic separation system (columns 5 to 7 and phase splitter tank). The separation system following the etherification reactor ensures the recycling of unconverted alcohols to the reactor (streams 10 and 19), and the distribution of olefins (streams 11, 23 and 32) and ethers (streams 7 and 8) such that the olefins are oligomerized, and collected ethers are used to produce a diesel blend. The oligomerization section is used to increase the molecular weight of the smaller olefins, such that the diesel yield increases. Additionally, a final fractionation area, shown in the figure as two distillation columns, is used. This is an exemplary implementation; other types of fractionation equipment can be used. In this area, all streams used for fuel production are fractionated into three products based on their initial boiling point: diesel #1, diesel #2, and gasoline.

Fuel Characterization

As shown in FIG. 13, the design includes a final purification/fractionation area to fractionate the final product into

#1 diesel, #2 diesel, and gasoline. The yield of #2 diesel via the present method is about 92%.

Methods

Guerbet coupling catalyst preparation: A 0.3% wt. $Cu/Mg_2{\cdot}9AlO$ catalyst was prepared through co-precipitation of $Cu(NO_3)_2{\cdot}3H_2O$ (Sigma-Aldrich, St. Louis, Missouri, USA, cat. #61194), $Al(NO_3)_3{\cdot}9H_2O$ (Sigma-Aldrich #237973) and $Mg(NO_3)_3{\cdot}6H_2O$ (Sigma-Aldrich #237175) precursors at pH 10. The resulting cake was filtered, washed with deionized water, dried overnight at 110° C. (Lab-line, 3511) and calcined for 2 h at 600° C. under heating ramp of 4° C. $min^{-1}$. A thorough description of the synthesis procedure accompanied with reagent proportions and catalyst characterization can be found in EIA, *Annual energy outlook* 2021, Washington DC, 2021, vol. 2021.

Hydrogenolysis catalyst preparation: Zirconia ($ZrO_2$) support was prepared through oxidative treatment of zirconium (IV) hydroxide ($Zr(OH)_4$, Aldrich #46417-1, 97%) as described in Davis et al. *Science* (1979), 2018, 360, 1419. Briefly, $Zr(OH)_4$ was calcined at 500° C. for 5 h on a 4° C. $min^{-1}$ heating ramp and static air atmosphere in a muffle furnace (ThermoFisher Scientific, Thermlyne) to obtain a white powder assumed to be zirconia ($ZrO_2$). Textural characterization by nitrogen physisorption was carried out in an ASAP 2020-brand device (Micromeritics, Norcross, Georgia, USA), yielding BET surface area of 146 $m^2$ $g^{-1}$ and BJH pore volume of 0.14 $cm^3$ $g^{-1}$. $Cu/ZrO_2$ catalyst with a theoretical metal load of 10% wt. was synthesized through incipient wetness impregnation by dissolving $Cu(NO_3)_2{\cdot}3H_2O$ (Sigma-Aldrich #61194, 99%) in an appropriate amount of Milli-Q water, heated up to 60° C. for a complete dissolution of the salt and added dropwise to the zirconia. After impregnation of the support, it was dried overnight (at least 12 h) in an oven at 110° C. and subsequently crushed and calcined (4° C. $min^{-1}$) at 500° C. for 5 h on a static air atmosphere.

Reaction conditions: Guerbet coupling and hydrogenolysis reactions were performed independently in the same reaction setup, thereby description of the reaction procedure varies only in reaction conditions. For sake of brevity, the reaction conditions for they hydrogenolysis are given first, in the main text; the conditions for the Guerbet coupling are given in square brackets. The calcined catalyst was sieved to 177-354 μm (mesh 80-45) and packed into a stainless-steel fix bed reactor (16-inch long, ⅜-inch outer diameter) by using 100-500 mg of the catalyst. Such powder was fixed at the center of the reactor by placing layers of glass wool (Acros Organics, #393611000) and silica chips (Sigma-Aldrich, 342831) at each end, and then reduced in situ at 300° C. (1° C./min) for 2 hours under 20 mL $min^{-1}$ of pure hydrogen flow (101 kPa) [325° C. (4° C. $min^{-1}$) for 12 hours under 50 mL $min^{-1}$ of pure hydrogen flow (101 kPa) 1 for Guerbet coupling]. Isothermal profile along the catalytic bed was attained by using aluminum blocks between the reactor and the electric tube furnace (Thermo Fisher, Lindberg blue M Mini-Mite); the temperature was measured with a K-type thermocouple, which was embedded in the aluminum heating block. After reduction, the reactor was cooled down to 200° C. and pressurized to 420 psig [325° C. and 300 psig] with a back-pressure regulator (Equilibar, ZF0SVN8). A blend of butanol-hexyl acetate of composition 95%-5% mol [ethanol–butanol 70%-30% mol], respectively, was fed with a syringe pump (Teledyne ISCO) at 6-18 μL min-1 [23-93 μL min-1], with pure $H_2$ cofeed at 36-109 mL min-1 [2.5-10.3 mL min-1] to a preheated section maintained at ~190° C. [>200° C.] to ensure feed was in gaseous phase when contacting the catalyst. The molar ratio of esters to hydrogen of the gaseous phase entering the reactor was kept constant at 1:480 for hydrogenolysis experiments, while for Guerbet coupling reactions the molar ratio of alcohols to hydrogen was maintained at 4:1. After reaction, products were collected in a removable 110 mL glass condenser (Ace glass) immersed in a dry ice bath. With the aim of reducing sampling error due to low product mass collection, 15 mL of 1-propanol (Sigma-Aldrich, #96566) was loaded to the condenser before collection of products with sample collection time of typically for 1-2 h. Gases that did not condense were sent to a three-valve, which led the gaseous flow to vent or towards an online gas GC (Shimadzu 2010) equipped with a flame ionization detector (FID) and thermal conductivity detector (TCD) for gas-phase sampling. Liquid samples were prepared to be analyzed through gas chromatography by diluting them with 1-propanol and adding a known amount of 1-pentanol as internal standard. Such liquid products were analyzed via GC-FID (Shimadzu 2014), and quantification was performed by using external standards. Product identity was further supported/confirmed by gas chromatography—mass spectrometry (Shimadzu GCMS-QP2010).

Etherification: The etherification of the ethanol/butanol Guerbet coupling products was carried out in an upward configuration continuous flow reactor made of stainless steel. The bed was packed with 1.8 g of powder HY catalyst (Si/Al=30). Ar gas was flowed at 10 mL/min, and the liquid flow rate was varied to obtain WHSV=1 $h^{-1}$. For determining cross-etherification species, the analytical techniques for product identification were also taken from Restrepo-Florez et al. 2023.

What is claimed is:

1. A process for making liquid fuels, the process comprising:

(a) subjecting a feedstock comprising primary alcohols to Guerbet coupling to yield a first intermediate mix comprising higher alcohols and byproducts comprising one or more compounds selected from the group consisting of esters, aldehydes, and ketones;

(b) subjecting at least a portion of the first intermediate mix to hydrogenolysis in the presence of hydrogen provided in excess relative to the byproducts, wherein at least a portion of any esters, aldehydes, and ketones present in the first intermediate mix are converted to their analogous alcohols, to yield a second intermediate mix;

(c) subjecting at least a portion of the second intermediate mix to etherifcation to yield a liquid fuel.

2. The method of claim 1, wherein in step (c), the etherification is conducted such that at least a portion of alcohols present in the second intermediate mix are converted to ethers.

3. The method of claim 1, wherein in step (b), at least a portion of unreacted primary alcohol is separated from the second intermediate product mix and recycled into the feedstock used in step (a).

4. The method of claim 1, wherein in step (a) the feedstock comprises ethanol; and wherein after step (b), at least a portion of unreacted ethanol and butanol are separated from the second intermediate product mix and recycled into the feedstock used in step (a).

5. The method of claim 1, further comprising fractionating the second intermediate mix into a heavy cut comprising alcohols having 10 or more carbon atoms and a light cut comprising alcohols having from 4 to 9 carbon atoms, and using the light cut as a feedstock for the etherification reaction of step (c).

6. The method of claim 5, further comprising combining the heavy cut with the liquid fuel from step (c).

7. The method of claim 1, wherein in step (a), the Guerbet coupling is conducting using a catalyst comprising an oxide selected from the group consisting of Mg, Ca, Zn, Mn, Sr, Si, Zr, Al, La, Ga, Ce, Fe, Sc, Cr, P, and V.

8. The method of claim 7, wherein the catalyst further comprises a metal selected from the group consisting of Cu, Ni, Pt, Pd, Rh, Co, Cs, and Rb.

9. The method of claim 1, wherein step (b), the hydrogenolysis is conducted using a catalyst comprising a metal selected from the group consisting of Cu, Ni, Rh, Ru, Ir, and Pd.

10. The method of claim 1, further comprising (d) oligomerizing at least a portion of olefins created by the etherification of step (c).

11. A process for making diesel fuel from ethanol, the process comprising:

(a) subjecting a feedstock comprising ethanol to Guerbet coupling to yield a first intermediate mix comprising butanol and byproducts comprising one or more compounds selected from the group consisting of esters, aldehydes, and ketones;

(b) subjecting at least a portion of the first intermediate mix to hydrogenolysis in the presence of hydrogen provided in excess relative to the byproducts, wherein at least a portion of any esters, aldehydes, and ketones present in the first intermediate mix are converted to their analogous alcohols, to yield a second intermediate mix;

(c) subjecting at least a portion of the second intermediate mix to etherifcation under conditions wherein at least a portion of alcohols present in the second intermediate mix are converted to ethers to yield diesel fuel.

12. The method of claim 11, wherein in step (b), at least a portion of unreacted methanol and a portion of butanol is separated from the second intermediate product mix and recycled into the feedstock used in step (a).

13. The method of claim 11, further comprising fractionating the second intermediate mix into a heavy cut comprising alcohols having 10 or more carbon atoms and a light cut comprising alcohols having from 4 to 9 carbon atoms, and using the light cut as a feedstock for the etherification reaction of step (c).

14. The method of claim 13, further comprising combining the heavy cut with the diesel fuel from step (c).

15. The method of claim 11, wherein in step (a), the Guerbet coupling is conducting using a catalyst comprising an oxide selected from the group consisting of Mg, Ca, Zn, Mn, Sr, Si, Zr, Al, La, Ga, Ce, Fe, Sc, Cr, P, and V.

16. The method of claim 15, wherein the catalyst further comprises a metal selected from the group consisting of Cu, Ni, Pt, Pd, Rh, Co, Cs, and Rb.

17. The method of claim 11, wherein step (b), the hydrogenolysis is conducted using a catalyst comprising a metal selected from the group consisting of Cu, Ni, Rh, Ru, Ir, and Pd.

18. The method of claim 11, further comprising (d) oligomerizing at least a portion of olefins created by the etherification of step (c).

* * * * *